US008951302B2

(12) United States Patent
Pryor et al.

(10) Patent No.: US 8,951,302 B2
(45) Date of Patent: Feb. 10, 2015

(54) BIOMIMETIC VASCULAR NETWORK AND DEVICES USING THE SAME

(75) Inventors: Howard I. Pryor, Washington, DC (US); Ira Spool, Newton, MA (US); David M. Hoganson, Boston, MA (US); Joseph P. Vacanti, Winchester, MA (US); Jeffrey T. Borenstein, Newton, MA (US)

(73) Assignees: The General Hospital Corporation, Boston, MA (US); The Charles Stark Draper Laboratory, Boston, MA (US)

( * ) Notice: Subject to any disclaimer, the term of this patent is extended or adjusted under 35 U.S.C. 154(b) by 980 days.

(21) Appl. No.: 12/576,826

(22) Filed: Oct. 9, 2009

(65) Prior Publication Data
US 2010/0234678 A1 Sep. 16, 2010

Related U.S. Application Data

(63) Continuation of application No. PCT/US2008/004872, filed on Apr. 14, 2008.

(60) Provisional application No. 60/923,312, filed on Apr. 12, 2007, provisional application No. 60/923,474, filed on Apr. 12, 2007.

(51) Int. Cl.
*A61F 2/04* (2013.01)
*A61F 2/06* (2013.01)
*G01N 33/50* (2006.01)

(52) U.S. Cl.
CPC ............ *A61F 2/062* (2013.01); *G01N 33/5008* (2013.01)
USPC ...................................... 623/23.65

(58) Field of Classification Search
None
See application file for complete search history.

(56) References Cited

U.S. PATENT DOCUMENTS 3,684,097 A    8/1972   Mathewson, Jr. et al.
3,839,204 A    10/1974  Ingenito et al.
(Continued)

FOREIGN PATENT DOCUMENTS

DE    10000823 A1    7/2001
EP    0246675 A1    11/1987
(Continued)

OTHER PUBLICATIONS

ISR for PCT/US2008/004872, Oct. 23, 2008, The General Hospital Corp.
(Continued)

*Primary Examiner* — Thomas J Sweet
*Assistant Examiner* — Rebecca Preston
(74) *Attorney, Agent, or Firm* — Edwards Wildman Palmer LLP; George N. Charles

(57) ABSTRACT

The invention provides method of fabricating a scaffold comprising a fluidic network, including the steps of: (a) generating an initial vascular layer for enclosing the chamber and providing fluid to the cells, the initial vascular layer having a network of channels for fluid; (b) translating the initial vascular layer into a model for fluid dynamics analysis; (c) analyzing the initial vascular layer based on desired parameters selected from the group consisting of a characteristic of a specific fluid, an input pressure, an output pressure, an overall flow rate and combinations thereof to determine sheer stress and velocity within the network of channels; (d) measuring the sheer stress and the velocity and comparing the obtained values to predetermined values; (e) determining if either of the shear stress or the velocity are greater than or less than the predetermined values, and (f) optionally modifying the initial vascular layer and repeating steps (b)-(e). The invention also provides compositions comprising a vascular layer for use in tissue lamina as well as a medical devices having a vascular layer and kits.

34 Claims, 12 Drawing Sheets

(56) References Cited

U.S. PATENT DOCUMENTS

| | | | |
|---|---|---|---|
| 3,892,533 | A | 7/1975 | Freedman et al. |
| 3,927,981 | A | 12/1975 | Viannay et al. |
| 3,977,976 | A | 8/1976 | Spaan et al. |
| 4,008,047 | A | 2/1977 | Petersen |
| 4,176,069 | A | 11/1979 | Metz et al. |
| 4,191,182 | A | 3/1980 | Popovich et al. |
| 4,229,290 | A | 10/1980 | Raj |
| 4,666,668 | A | 5/1987 | Lidorenko et al. |
| 5,034,188 | A | 7/1991 | Nakanishi et al. |
| 5,110,548 | A | 5/1992 | Montevecchi et al. |
| 5,222,982 | A | 6/1993 | Ommaya |
| 5,225,161 | A | 7/1993 | Mathewson et al. |
| 5,263,924 | A | 11/1993 | Mathewson |
| 5,308,356 | A | 5/1994 | Blackshear, Jr. et al. |
| 5,316,724 | A | 5/1994 | Mathewson et al. |
| 5,601,727 | A | 2/1997 | Bormann et al. |
| 5,626,759 | A | 5/1997 | Krantz et al. |
| 5,695,717 | A | 12/1997 | Polaschegg et al. |
| 6,022,743 | A | 2/2000 | Naughton et al. |
| 7,048,856 | B2 | 5/2006 | Fissell, IV et al. |
| 7,191,110 | B1 | 3/2007 | Charbel et al. |
| 7,727,339 | B2 | 6/2010 | Kapoor et al. |
| 7,955,504 | B1 | 6/2011 | Jovanovic et al. |
| 8,128,822 | B2 | 3/2012 | Browning et al. |
| 8,137,554 | B2 | 3/2012 | Jovanovic et al. |
| 2002/0106311 | A1 | 8/2002 | Golbig et al. |
| 2002/0182241 | A1 | 12/2002 | Borenstein et al. |
| 2003/0075498 | A1 | 4/2003 | Watkins et al. |
| 2003/0129736 | A1 | 7/2003 | Mitrani |
| 2004/0057869 | A1 | 3/2004 | Dingley |
| 2005/0202557 | A1 | 9/2005 | Borenstein et al. |
| 2006/0018838 | A1 | 1/2006 | George et al. |
| 2006/0136182 | A1 | 6/2006 | Vacanti et al. |
| 2006/0278580 | A1 | 12/2006 | Striemer et al. |
| 2007/0125489 | A1 | 6/2007 | Paul et al. |
| 2007/0128171 | A1 | 6/2007 | Tranquillo et al. |
| 2007/0243574 | A1 | 10/2007 | Williams et al. |
| 2009/0053752 | A1 | 2/2009 | Blackman et al. |
| 2010/0100027 | A1 | 4/2010 | Schilthuizen et al. |
| 2010/0326914 | A1 | 12/2010 | Drost et al. |
| 2010/0326916 | A1 | 12/2010 | Wrazel et al. |
| 2012/0074062 | A1 | 3/2012 | Jovanovic et al. |

FOREIGN PATENT DOCUMENTS

| | | |
|---|---|---|
| JP | 60-181654 A | 9/1985 |
| JP | 6237992 | 8/1994 |
| WO | WO-0038758 A1 | 7/2000 |
| WO | WO-02076529 A1 | 10/2002 |
| WO | WO-03082145 A2 | 10/2003 |
| WO | WO-2004026115 | 4/2004 |
| WO | WO-2007119073 A1 | 10/2007 |
| WO | WO-2009/102751 | 8/2009 |

OTHER PUBLICATIONS

Written Opinion for PCT/US2008/004872, Oct. 23, 2008, The General Hospital Corp.
Form PCT/ISA/210, Sep. 25, 2009, ISR for PCT/US2009/033736.
ISR for PCT/US2008/004872, Oct. 23, 2008, The Gen Hospital Corp.
Written Opinion for PCT/US2008/004872, Oct. 23, 2008, The Gen Hospital Corp.
Kane, R.S. et al. Patterning proteins and cells using soft lithography. Biomaterials. 1999.20: 2363-2376.
Fidkowski, Christina, et al., Endothelialized Microvasculature Based on a Biodegradable Elastomer, Tissue Engineering, vol. 11, No. 1/2, 2005, pp. 302-309.
Hupert, Mateusz L., et al., Evaluation of micromilled metal mold masters for the replication of microchip electrophoresis devices, Microfluid Nanofluid (2007) 3:1-11.
Fanucci, Ezio, et al., Optimal Branching of Human Arterial Bifurcations, Institute of Radiology and the Section of Medical Physica, II University of Rome, Tor Vergata, Roma, Italy, Jan. 1990, pp. 62-66.
Malek, Adel M., et al., Hemodynamic Shear Stress and Its Role in Atherosclerosis, JAMA, Dec. 1, 1999, vol. 282, No. 21, pp. 2035-2042.
Dammers, Ruben, et al., Shear stress depends on vascular territory; comparison between common carotid and brachial artery, J Appl Physiol 94: 485-489, 2003.
Zamir, M. et al., Arterial Branching in Various Parts of the Cardiovascular System, The American Journal of Anatomy 163: 295-307 (1982).
Wootton David M. et al., Fluid Mechanics of Vascular Systems, Diseases, and Thrombosis, Annu. Rev. Biomed. Eng. 1999. 01:299-329.
Sherman, Thomas F., On Connecting Large Vessels to Small, J. Gen. Physiol., vol. 78, Oct. 1981, 431-453.
Borenstein, et al: "Microfabrication technology for vascularized tissue engineering." Biomedical Microdevices Kluwer Academic Publishers, USA, vol. 4, No. 3, Jul. 2002 (Jul. 2001), pp. 167-175.
Cross "Fractals in Pathology." Journal of Pathology 182: 1-8 (1997).
Anderson et al. "Fabrication of Topologically Complex Three-Dimensional Microfluidic Systems in PDMS by Rapid Prototyping." Anal. Chem 72: 3158-3164 (2000).
Hediger et al. "Biosystem for the Culture and Characterisation of Epithelial Cell Tissues." Sensors and Actuators B 63: 63-73 (2000).
Borenstein et al. "Living Three-Dimensional Microfabricated Constructs for the Replacement of Vital Organ Function." Transducers 4C1.3: 1754-1757 (2003).
Stone "Microfluidics: Basic Issues, Applications, and Challenges." American Institute of Chemical Engineers Journal 47(6): 1250-1254 (2001).
Fairley "Blood from a Chip." Technology Review, p. 28 (2000).
Borenstein et al: "Microfabrication of Three-Dimensional Engineered Scaffolds". Tissue Engineering, vol. 13, No. 8, 2007, pp. 1837-1844.
Emerson et al: "Biomimetic Design of Microfluidic Manifolds Based on a Generalised Murray's Law". The Royal Society of Chemistry 2006, Lab Chip, 2006, 6, 447-454.
Roush "BioEngine: One Step Closer to Artificial Liver Device". http://www.xconomy.com/2007/09/20/bioenpine-one-step-closer-to-artificial-liver-device/; Sep. 20, 2007.
Fischer "The Novalung® iLA membrane ventilator: technical aspects"; http://www.ctsnet.org/sections/portals/thoracic/newtechnology/article-9.html; Last viewed online on Mar. 19, 2008.
Lim, et al., Lab Chip (2003), 3: 318-323.
Iwasaki et al., Science Direct (Aug. 2), 23/16: 3421-3427.
Biomedical Materials; Polyimide membrane for use as artificial lung material, http://www.highbeam.com/doc/1G1-45103565 (Nov. 1, 1994).
Membrana "Oxygenerator"; http://www.membrana.com/oxygenation/hexpet/center.htm; Last viewed online on Mar. 19, 2008.
Mengoli "Creation and working of an oxygenator, industrial view"; http://www.sciencedirect.com/; Dec. 2006, pp. S14-S15.
Nichols et al, McDonald's Blood Flow in Arteries, 5th Edition, Chapter 2, "The nature of flow of a liquid", pp. 11-48 (1998).

BIOMIMETIC VASCULAR NETWORK AND DEVICES USING THE SAME

RELATED APPLICATIONS

This application is a continuation of PCT international application Ser. No. PCT/US2008/004872, filed Apr. 14, 2008, designating the United States and published in English on Oct. 23, 2008 as publication WO 2008/127732 A3, which claims priority to U.S. Provisional Application Ser. No. 60/923,312, filed Apr. 12, 2007 and U.S. Provisional Application Ser. No. 60/923,474, filed Apr. 12, 2007. The entire contents of the aforementioned patent applications are incorporated herein by this reference.

STATEMENT OF GOVERNMENT SUPPORT

Some of the work described herein was sponsored by the National Institutes of Health, Grant Nos. 1 F32 DK076349-01 and T32DK07754-09. The U.S. Government has certain rights in this invention.

BACKGROUND OF THE INVENTION

Although organ transplantation has emerged as viable treatment for patients with end stage organ disease, there is a uniform organ shortage in the United States and worldwide. Patients awaiting liver, lung and heart transplants often die before they receive an organ due to the long transplant waiting times. Artificial organs could be used to assist or even replace organs as a solution to the organ shortage.

Development of a tissue engineered solid organ such as a liver or kidney is typically dependent on two main components—the parenchymal cells and a vascular network to supply oxygen and nutrients to the parenchymal cells. The diffusion distance of oxygen and nutrients from a blood vessel through tissue is very short (e.g., a few hundred microns). If cells, such as hepatocytes are grown in a three-dimensional container and placed in the body near a blood vessel, only the cells in close proximity to the blood vessel will survive. Over time, new blood vessels may grow into the implanted cells, however, many of the cells that are far from the existing blood vessels will die without immediate blood supply.

Present designs provide a vascular network as a central part of the scaffold for a tissue engineered solid organ. The vascular network serves as the blood supply to deliver oxygen and nutrients to the other cells which are also placed in the scaffold to give the organ its function (e.g., hepatocytes for a tissue engineered liver). This approach allows a vascular network to be designed for the particular organ from the inlet vessels which are anastomosed to the native circulation to the smallest vessels which perfuse the parenchymal cells. This tissue engineered organ is implanted with blood vessels already adequately located in proximity to the parenchymal cells. This allows a thick, solid organ such as the liver, lung, heart, kidney or other organs or tissues to be created and implanted.

In the body, blood vessels which supply organs typically enter the organs as one single vessel (typically an artery) and then branch in a pattern, reducing their diameter and greatly increasing their surface area until they form the smallest vessels known as capillaries. The capillaries supply the cells of the organ with oxygen and nutrients and remove waste products. From the capillaries, the vessels coalesce in a similar branching pattern to exit the organ often as a single vessel (typically a vein). There is a need in the art for tissue engineered organs having such a physiological vasculature network to provide sustained function following implantation.

SUMMARY OF THE INVENTION

It is an object of the subject technology to provide a tissue engineered organ which has a structure similar to natural organs and is capable of similar performance for sufficient periods of time without malfunction. Preferably, the tissue engineered organ will have low thrombogenicity and a high packing efficiency.

It is envisioned that the subject technology may be used to replace an organ, in vivo or ex vivo, assist an organ, temporarily replace an organ and ascertain the efficacy and safety of a drug on human cells.

One aspect of the subject technology provides a method of fabricating a scaffold comprising a fluidic network. The method includes the steps of: (a) generating an initial vascular layer for enclosing the chamber and providing fluid to the cells, the initial vascular layer having a network of channels for fluid; (b) translating the initial vascular layer into a model for fluid dynamics analysis; (c) analyzing the initial vascular layer based on desired parameters selected from the group consisting of a characteristic of a specific fluid, an input pressure, an output pressure, an overall flow rate and combinations thereof to determine sheer stress and velocity within the network of channels; (d) measuring the sheer stress and the velocity and comparing the obtained values to predetermined values; (e) determining if either of the shear stress or the velocity are greater than or less than the predetermined values, and (f) optionally modifying the initial vascular layer and repeating steps (b)-(e). The initial vascular layer may be fabricated from collagen.

Another aspect of the subject technology is directed to a composition comprising a vascular layer for use in a tissue lamina. The vascular layer includes a substrate defining a network of channels having at least one input channel and at least one output channel and at least two intermediate channels at least partially connecting the at least one input channel and the at least one output channel, each channel having a height and a width, wherein the intermediate channels are formed in accordance with Murray's law by varying said height and width with respect to adjacent portions of the input and output channels.

The subject technology also provides an artificial vascular network including a substrate defining a network of channels having at least one input channel and at least one output channel and at least two intermediate channels at least partially connecting the at least one input channel and the at least one output channel. Each channel has a height and a width, wherein the intermediate channels are formed in accordance with Murray's law by varying said height and width with respect to adjacent portions of the input and output channels. The artificial vascular network is prepared by a process including the steps of: (a) fabricating a substrate defining a network of channels, wherein the channels provide fluid to cells; (b) translating the network of channels into a model for fluid dynamics analysis; (c) analyzing the network of channels based on desired parameters selected from the group consisting of a characteristic of a specific fluid, an input pressure, an output pressure, an overall flow rate and combinations thereof to determine sheer stress and velocity within the network of channels; (d) measuring the sheer stress and the velocity and comparing the obtained values to predetermined values; and (e) determining if either of the shear stress or the velocity are greater than or less than the predetermined values.

Another aspect is a medical device for assisting or replacing an organ including a header layer having a nozzle to connect to a vessel and defining a distribution network in fluid communication with the nozzle, and a first vascular layer having a substrate defining a vascular network of channels in fluid communication with the distribution network, the vascular network including at least one input channel that bifurcates repeatedly into portions, which rejoin to form an output channel, the input and output channels having a height and a width, wherein the bifurcated portions are formed in accordance with Murray's law by varying said height and width with respect to adjacent portions of the input and output channels. Another layer defines a chamber for holding parenchymal cells that is configured to receive oxygen and nutrients from a fluid in the vascular layer.

A membrane separates the vascular layer from the parenchymal chamber. Preferably, the membrane is semi-permeable and the pore size of the membrane is smaller than the cell diameters, thus, cells will not be able to pass through (i.e., a low permeability for animal cells), while low molecular weight nutrients, gases and fluids can pass through (i.e., a high permeability for small compounds), thereby providing adequate cell-to-cell signaling. Cell sizes vary but in general, the cell sizes are in the range of microns. For example, a red blood cell has a diameter of about 8 µm. Preferably, the average membrane pore size is on a submicron-scale to ensure effective screening of the cells. For lung application and the like, the membrane should also allow passage of carbon dioxide, oxygen and like gases therethrough.

A vascular network for creating tissue engineered organs in accordance with the subject technology follows the same approach as the blood vessels within a natural organ. The replication of physiological design principles in vascular networks is referred to herein by the phrase "biomimetic vascular networks".

The subject technology described herein includes the theory, concepts, design, manufacturing, testing and applications of biomimetic vascular networks. These vascular networks have primary application as a central part of a scaffold to create a tissue engineered structure such as an organ or other mammalian tissue. There are additional applications of this technology, for example, as a tool, e.g., a platform for drug discovery, development and/or evaluation (e.g., toxicity, safety and/or efficacy) and as a platform for in vitro or in vivo research and testing.

It should be appreciated that the present invention can be implemented and utilized in numerous ways, including without limitation as a process, an apparatus, a system, a device, a kit (e.g., a kit comprising one of the platforms described herein and instructions for use), a method for applications now known and later developed or a computer readable medium. These and other unique features of the system disclosed herein will become more readily apparent from the following description and the accompanying drawings.

BRIEF DESCRIPTION OF THE DRAWINGS

Other aspects and many of the attendant advantages of this invention will readily be appreciated as the same becomes better understood by reference to the following detailed description when considered in connection with the accompanying drawings wherein.

DETAILED DESCRIPTION OF PREFERRED EMBODIMENTS

Figure 1:
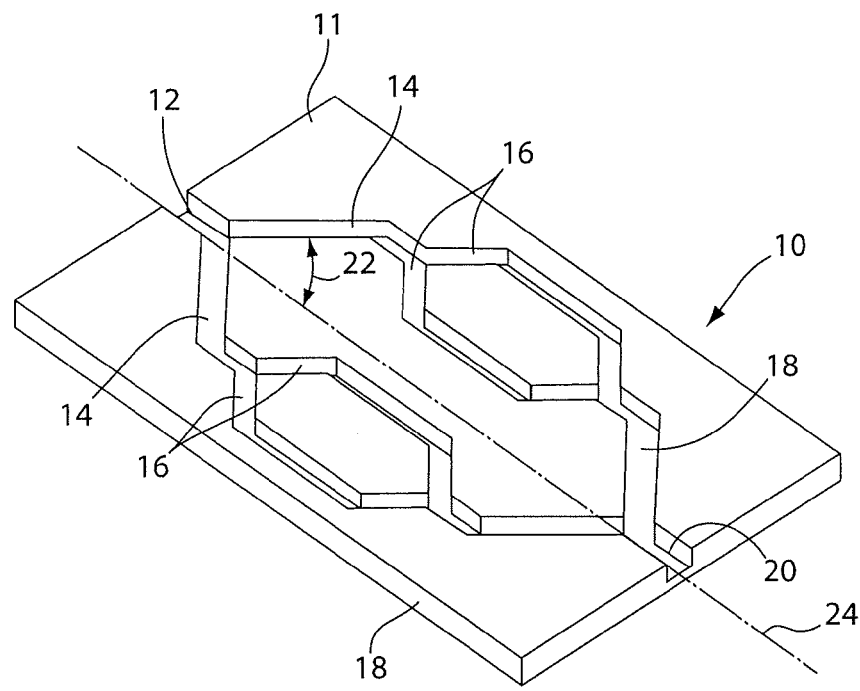
FIG. 1 illustrates a perspective view of a bifurcating portion of a vascular network in accordance with the subject technology.

The present invention overcomes many of the prior art challenges associated with tissue engineered vascular networks and artificial solid organs. The advantages, and other features of the technology disclosed herein, will become more readily apparent to those having ordinary skill in the art from the following detailed description of certain embodiments taken in conjunction with the drawings which set forth representative embodiments of the present invention and wherein like reference numerals identify similar structural elements.

It is to be understood that the subject technology is not intended to be limited to the particular constructs and methods described in the described embodiments, as one skilled in the art can extend the concepts involved using variations which are obvious after reading the present disclosure. Although any methods and materials similar or equivalent to those described herein may be useful in the practice of the subject technology, certain compositions, films, methods and materials are described below. All relative descriptions herein such as top, bottom, left, right, up, and down are with reference to the Figures, and not meant in a limiting sense.

The process of creating an optimal vascular network design that performs sufficiently is aided by identifying and learning from the fundamental structure of blood vessels in the body. The vascular network of arteries, capillaries and veins is complex. However, the basic structural principles can be utilized within the limits of currently available manufacturing processes. There are several fundamental principles of blood vessels which have been utilized in the subject technology and incorporated into the design of the biomimetic vascular networks described herein. The concepts and the resulting designs are also advantageously refined using computational fluid dynamics (CFD) analysis.

Blood vessels in the body have a particular relationship between the diameter of a parent vessel and the diameters of the resulting daughter vessels known as Murray's Law. Generally, Murray's Law states that the cube of the diameter of the parent vessel is equal to the sum of the cubed diameters of all daughter vessels. For a bifurcating channel, Murray's Law is expressed as $d_0^3 = d_1^3 + d_2^3$, where $d_0$ is the diameter of the parent vessel and $d_1$ and $d_2$ are the diameters of the daughter vessels. The reference of diameter in regard to a rectangular channel refers to the hydraulic diameter of the channel as defined as hydraulic diameter=4*(cross-sectional area of channel)/(channel perimeter).

The principle of Murray's law was described in the 1930's and has since been confirmed in many studies. The principle of Murray's law is to optimize the efficiency of mass transport of the blood and control the shear stress within the vessels or channels. Shear stress in blood vessels within the body is tightly controlled within a physiologic range. Shear stress for arteries is typically on the range of 15 to 70 dynes/cm$^2$ and for veins the shear stress is typically on the range of 1-5 dynes/cm$^2$. Vessel bifurcations have shear stress which is fairly uniform over the entire network.

Controlling shear stress is very important in minimizing the formation of thrombus within the network and ensuring that oxygen and nutrient exchange occurs within normal physiologic parameters. The biomimetic principle of designing for appropriate shear stress was employed in the design of the vascular networks described herein to reduce or eliminate thrombosis with the networks.

A Vascular Network Design

Referring to FIG. 1, a bifurcating portion 10 of a representative simple vascular network is shown in perspective view. The network portion 10 includes a substrate 11 having channels formed therein. A parent vessel or channel 12 bifurcates into two daughter vessels 14. According to Murray's law, if the daughter vessels 14 are equal, then Murray's law simplifies to $d_0^3 = 2(d_1^3)$. For example, if the parent vessel 12 is 1000 um in diameter than each of the daughter vessels 14 would be 794 um in diameter. The daughter vessels 14 further bifurcate into smaller vessels 16. According to Murray's law, the resulting smaller vessels 18 and 20 would be 630 um in diameter for this example.

The smaller vessels 16 rejoin to form a larger vessels 18, which then join to form vessel 20. In one embodiment, the smaller vessels 16 are most representative of the capillary vessels found in the body. However, the parent channels 12, 14 may participate in nutrient, gas, and waste exchange in a similar manner as the smallest channels 16. Likewise the channels 18, 20, which are formed from the smallest channels 16, are somewhat analogous to capillaries or venules or veins in the body. Similarly, the channels 18, 20 may also participate in nutrient, gas and waste exchange like the smallest channels 16.

The vessels 12, 14, 16, 18, 20 are formed from linear structures and substantially rectangular. In another embodiment, the vessels 12, 14, 16, 18, 20 may be circular or elliptical nature. In the event that the vessels 12, 14, 16, 18, 20 are rectangular, the vessels 12, 14, 16, 18, 20 may have an aspect ratio of 1:1, e.g., the width and depth are equal. In another embodiment, the vessels 12, 14, 16, 18, 20 may have an aspect ratio of: 1:2; 2:1; or the like. Furthermore any aspect ratio such as the range of 100:1 or 1:100 may be considered depending on the particular application of the vascular network.

Figure 2:
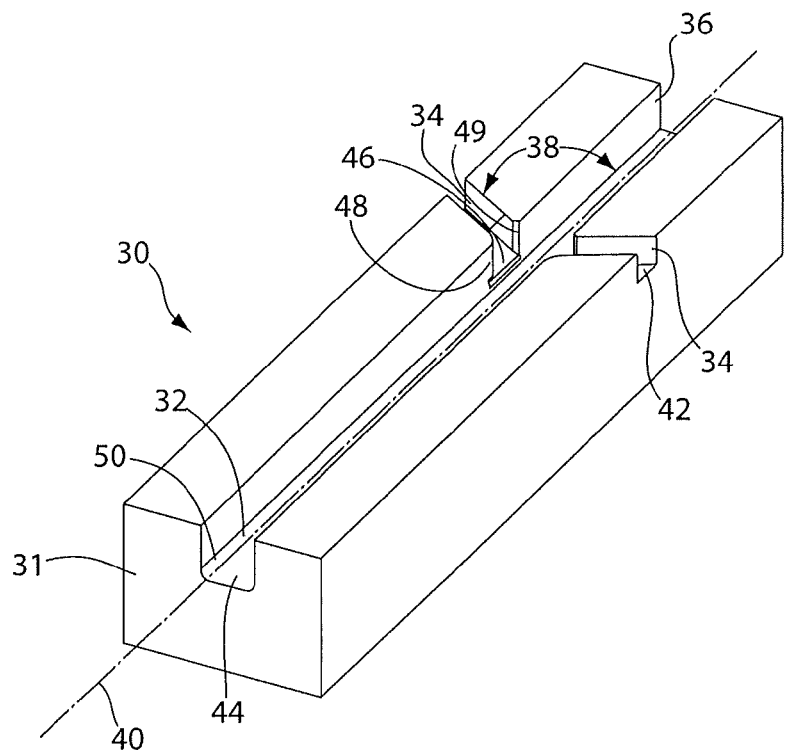
FIG. 2 illustrates a perspective view of a trifurcating portion of a vascular network in accordance with the subject technology.

Referring to FIG. 2, a perspective view of a trifurcating portion 30 of a vascular network is shown. The trifurcating portion 30 also includes a substrate 31 that forms a parent vessel 32, which divides into two equal daughter vessels 34 and a larger daughter vessel 36 as commonly occurs in the body. In this event, Murray's law is $d_0^3 = d_1^3 + d_2^3 + d_3^3$. Preferably, Murray's law is applied so as to achieve an adequate capillary channel density so the maximum distance between channels 32, 34, 36 does not exceed the maximum diffusion distance of oxygen and nutrients.

In one embodiment, the maximum distance between channels would not exceed 40 um. In another embodiment this maximum distance would not exceed 500 um. In another embodiment, this maximum distance would be in the range of 200 um to 300 um. In another embodiment, a majority of the channels would fall within a maximum distance and a minority of the channels would have a distance therebetween higher than the preferred maximum. A network needs to both follow or approximate Murray's law and the other design principles described herein and achieve a branching strategy which results in achievement of the desired maximum distance between channels.

Generally, the bifurcation angle between the parent vessel and the daughter vessels in the body is related to the relative diameters of the daughter vessels. These relations are described in the literature. In principle, if there are two daughter vessels 14 which are equal in diameter as shown in FIG. 1, the preferred angle 22 between an axis 24 of the parent vessel 12 and the daughter vessel is approximately 45 degrees.

Still referring to FIG. 2, when one or two daughter vessels 34 are smaller than another daughter vessel 36, the preferred angle 38 between the axis 40 of the parent vessel 32 and the daughter vessels 34 becomes larger than 45 degrees and approaches 90 degrees as the daughter vessels 34 become much smaller than the parent vessel 32 and other daughter vessel 36. Following these biomimetic principles of bifurcation angles helps to achieve uniform blood flow with minimal shear disruption and hence platelet activation.

In the embodiment of FIG. 2, the smaller daughter channels 34 are orientated such that a bottom 42 of the channel 34 is not on the same plane with respect to the bottom 44 of the parent channel 32 but the respective tops of channels 32, 34 are on the same plane. As a result, an edge 46 is created in the transition between channels 32, 34. Additionally, vertical edges 48 are created in the same transition. The edges 46, 48 are potential area for shear stress concentrations, flow separation, stasis or turbulence within the device.

Still referring to FIG. 2, the bottom 44 of the parent channel 32 includes a radius of curvature or fillet 50 on each side. In the absence of a radius of curvature 50, there is lower blood velocity in the corner area than in other portions of the channel 32. The addition of the fillets 50 creates a more uniform velocity in the channel 32.

The size, shape and position of the fillets 50 are selected using computational fluid dynamics (CFD) analysis, which is a tool used to analyze fluid flow to predict the behavior of a fluid within a defined model. One version of a CFD tool is the FLOWORKS® module within the SOLIDWORKS® 3D CAD software available from SolidWorks Corporation of Concord, Mass. The vascular network designs are modeled in three dimensions and then analyzed with CFD analysis to iterate and evaluate performance of the features with respect to selected parameters.

Modification of the design elements of the networks from known biomimetic principles may occur, however there are goals or criteria of the flow of fluid through the network which are established and used as a guideline or boundary condition. For example, target shear stress, inlet pressure, outlet pressure and resulting flow rate can be the primary goals of the design. Other goals of the design may include minimizing flow separation, minimizing areas of low flow velocity and/or stagnation.

In one embodiment, the boundary conditions defined for the CFD analysis of the network are a combination of inlet pressure, outlet pressure and flow rate. The analysis focuses on blood in a non-Newtonian model as the fluid flowing through the vascular network. After the CFD module completes the analysis, the results are reviewed, specifically the pressure drop across the network, the flow within the network, the shear stress on all of the walls of the network, and the velocity within the channels including the uniformity of velocity. If any of the parameters fall outside a target range, then the design is modified and the analysis is repeated.

For example, if the shear stress within a certain area is too high, that area of the design is modified and the analysis run again. The iterative sequence of reviewing an analysis, determining an area of the design which is not optimal, changing the design and running the analysis again is repeated to optimize many of the features of the design. For example, the fillet or defined curvature of each edge for optimal flow can be varied in response to CFD analysis. Referring again to FIG. 2, the dimensions of the fillets 50 relative to that of the channel 32 were optimized using CFD analysis.

Furthermore, the fillets 46, 48 and 49 in the transition between channel 32 and channel 34 are each different parameters. Serial iterations of design changes, CFD analysis and review of results can optimize not only each fillet but the bifurcation as a unit so the flow at the convergence of channels 32, 34 and 36 is uniform with minimal shear stress changes and, thus, minimal risk for blood clot formation. As a result of the iterative process, branching channel design can be formed with minimal flow disturbances.

Figure 3:
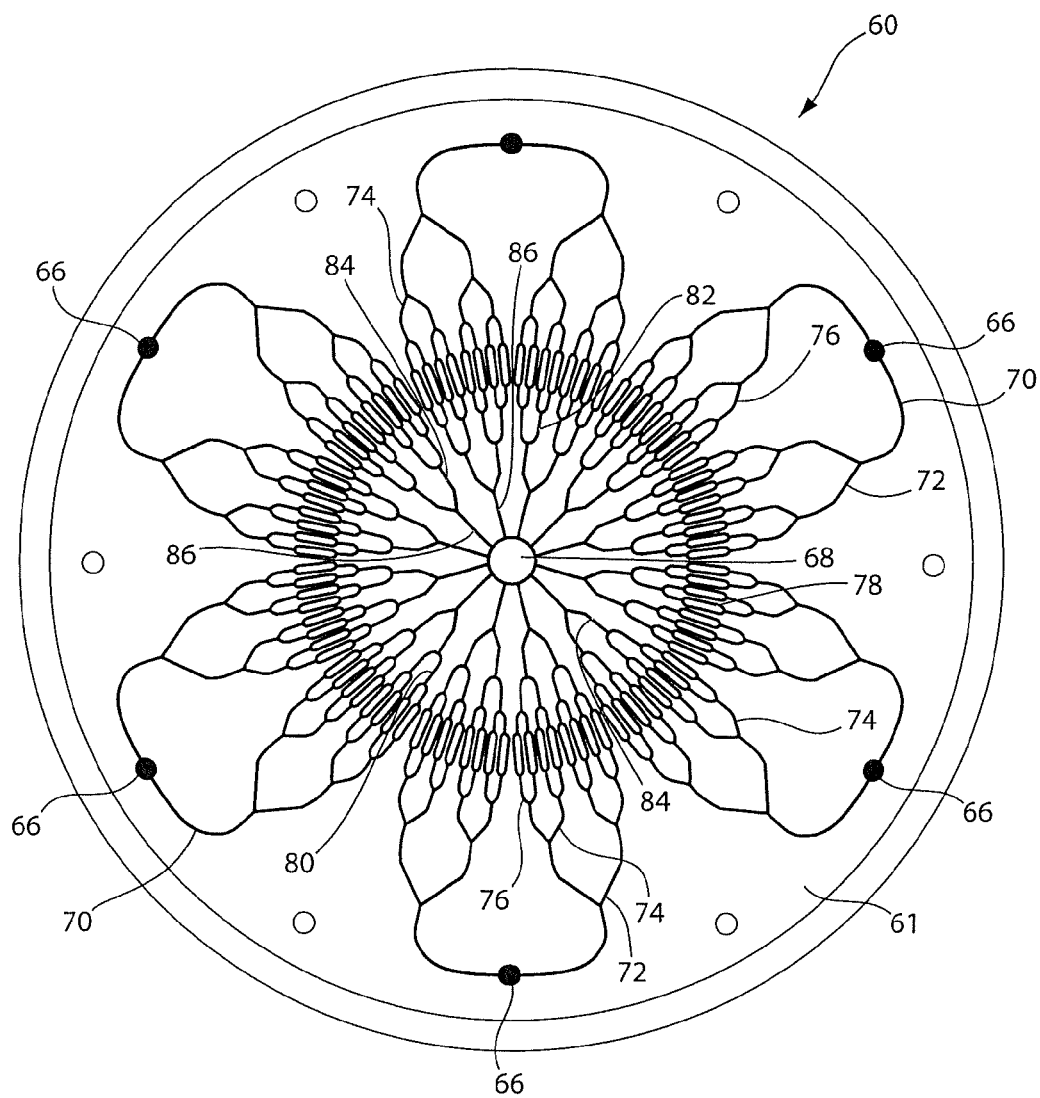
FIG. 3 is a top view of a vascular network design in accordance with the subject technology.
Figure 4:
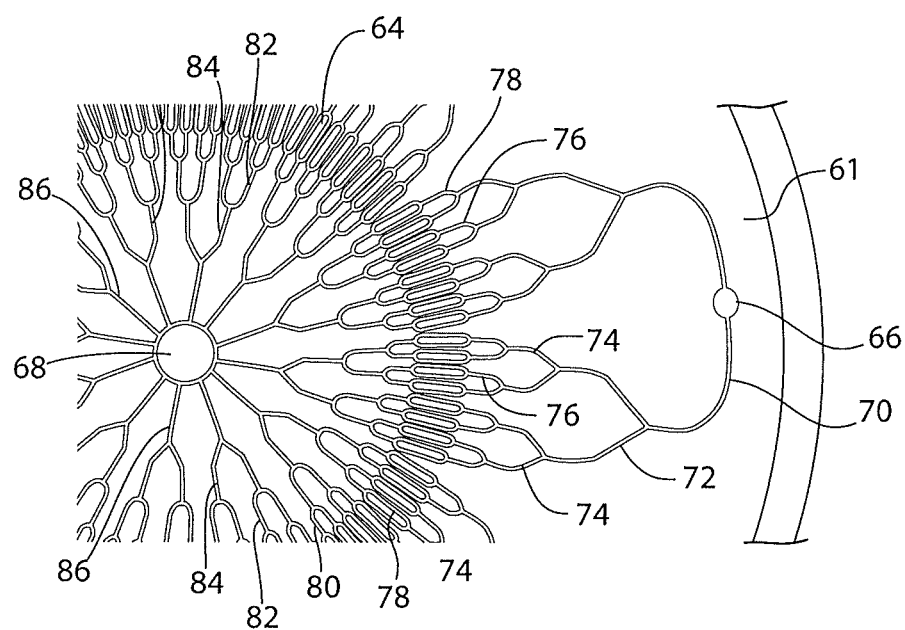
FIG. 4 is a more detailed top view of a portion of the vascular network design of FIG. 3.

Referring now to FIGS. 3 and 4, top views of a vascular network design 60 are illustrated. The vascular network design 60 replicates the basic structure of the vascular system of the liver, which is arranged in a radial hexagonal pattern. The vascular network design 60 includes a substrate 61 forming channels 62 with hexagonal areas or liver lobules 64 (best seen in FIG. 4) intermediate the channels 62. Each hexagonal area of a liver has several (usually six) blood vessels at the periphery of the lobule which undergo branching toward a central vein. The basic design for the vascular network design 60 was organized similar to a liver lobule. The vascular network design 60 has six radially spaced inlet channels 66 which undergo multiple bifurcations towards a central draining vein 68.

Unlike the liver lobule, which is a tightly packed structure of blood vessels and cells, one can clearly observe that in certain points of the vascular network design 60, there is a significant distance between adjacent channels. A goal of the vascular network design 60 was to take a step towards the fundamental structure of a liver lobule but keep the vascular network branching pattern simple to understand the utility of the biomimetic design principles. Other designs may pursue a much denser pattern to achieve effective delivery of oxygen and nutrients.

Accordingly, in the planar vascular network design 60 of FIG. 3, the inlet channels 66 and outlet central vein 68 are oriented orthogonal to the branching channels 62. The channels 62 are rectangular with an aspect ratio of 1:1 and hydraulic diameters calculated according to Murray's law. The channels 62 start with initial channels 70 in fluid communication with the inlet channels 66. The initial channels 70 successively branch, in a bifurcating manner, into successively smaller channels 72, 74, 76, 78. The smallest diameter channels 78 are preferably 200 um in diameter while the initial channels 70 from the inlet are 608 um in diameter. Since the channels 62 undergo simple bifurcations, the bifurcation angles are 45 degrees for each. Similarly, the channels 62 rejoin to form successively larger channels 80, 82, 84, 86, which also have bifurcation angles of 45 degrees with the largest rejoining channels 86 being in fluid communication with the outlet central vein 68.

Generally, in the body, the smaller the blood vessel diameter, the shorter the blood vessel, with capillaries being the shortest blood vessels. More specifically, the literature enumerated lengths of several vessels according vessel diameter from 4 mm diameter arteries to 8 um diameter capillaries. Using this data in a spreadsheet program, a $3^{rd}$ order polynomial equation was determined through best fit analysis to derive a biomimetic length for the different diameter channels in the vascular network design 60. For a blood vessel of diameter x, the length y was determined by the equation, $y=(-1*10^{-9}*x^3)+(8*10^{-06}*x^2)+(0.0259*x)+0.1226$.

For the vascular network design 60, the smallest channels 78 were 200 um in diameter and the biomimetic length derived from the previously stated equation was used to determine a biomimetic length of 6.79 mm. The branches 70, 72, 74 and 76 which preceded the smallest channel 78 and the branches 80, 82, 84, and 86 which followed, could not be constructed with their biomimetic lengths due to the size constraints of the mold. Therefore, the biomimetic length of the smallest channel 78 was used and the lengths of the other channels (70, 72, 74, 76, 80, 82 and 84) were scaled to 39.2% of their biomimetic length to enable the entire vascular network to fit within the defined mold size of six inches in diameter. Thus, the vascular network design 60 uses proportionally smaller lengths while preserving length relationships between channels of different diameters. In another embodiment, the biomimetic lengths of all of the channels could be scaled in an equal fashion.

The shear stress in arteries is between 15 and 70 dynes/$cm^2$. The channels 62 are designed in response to blood flow under CFD analysis to form curves which minimize concentrations of shear stress. Through an iterative design process using results from repeated CFD analysis, the curvature of the vascular network design 60 was improved to minimize concentrations of shear stress. The vascular network design 60 also keep at least some of the input channels 70, 72, 74, 76, 78 in the physiological shear stress range for arteries. Additionally, as described above, the channels 62 may have radii of curvature or fillets, particularly at the points of bifurcation, to improve the flow characteristics. In short, all of the channels 62 can be evaluated and refined using results from repeated CFD analysis to minimize the variation of shear stress.

The venous system in the body has comparatively larger diameters and lower shear stress than the arterial system. Accordingly, the shear stress within the venous system is typically 1 to 5 dynes/$cm^2$, which is lower than the shear stress in the arterial system. The vascular network design 60 has lower shear stress in the output channels 80, 82, 84, 86 to minimize resistance and mimic the venous shear stress values. There is a balance between achieving a low shear stress value to replicate the human veins and having too slow of blood flow such that thrombus may be initiated. Thus, the output channels 80, 82, 84, 86 are scaled up in diameter compared to the inlet channels 70, 72, 74, 76, 78 to achieve a shear stress value of generally between 6 and 10 dynes/cm$^2$.

In other embodiments, the shear stress values for the inflow portion of a vascular network may correspond to normal arterial shear stress values and the outflow portions of the network may correspond to normal venous shear stress values. The degree of scaling up of the diameters of the venous system may be in the range of 1% to 50% of the corresponding inflow diameters. In another embodiment, the degree of venous scaling may be in the range of 5% to 15% of the corresponding venous diameters. Although the vascular network design 60 has a branching pattern in the outflow portion which closely replicates the branching pattern in the inflow portion, in other embodiments, the branching pattern of the inflow and outflow portions may not be similar. Furthermore, the branching pattern between portions of the inflow areas of the network may be different than other areas of the inflow network. Likewise in other embodiments, the branching pattern between portions of the outflow areas of the network may be different than other areas of the outflow network.

Process for Creating the Vascular Network Design

Previous vascular networks for tissue engineered organ development were manufactured utilizing molds created using the photolithography process and replica casting using silicone as described in U.S. patent application Ser. No. 10/187,247, filed Jun. 28, 2002 and U.S. patent application Ser. No. 10/983,213, filed Nov. 5, 2004. Photolithography is only able to create a single depth of channel or multiple depths with vertical step transitions. In contrast, the vascular network design 60 has many different diameters of channels and these channels may achieve the most uniform blood flow if the channels have an aspect ratio not equal to 1:1. Furthermore, a uniform depth transition between the channels can minimize shear stress changes. Minimizing shear stress changes and associated flow disturbances will minimize clotting within the resulting device. In this regard, the device can be characterized as have low thrombogenicity.

Although using photolithography to create a mold to manufacture the vascular network design 60 is possible, a different manufacturing process was used, namely electrical discharge machining (EDM) or micro-machine tool equipment available from Microlution, Inc. of Chicago, Ill. In the EDM process, an electrode in the shape of the reverse or mirror image of the vascular network design 60 is created out of graphite using traditional milling machining processes. The electrode is then used to vaporize metal in the desired pattern to create a metal or vascular mold (not shown). The mold is preferably a positive mold, thus the channel features are ridges projecting from a base. To create the vascular network design 60, a material is placed over the mold in a manner in which the material takes the shape of the projected network pattern. The mold is then removed from the material or substrate 61, leaving the imprint of the vascular network design 60 in the material.

The Assembled Implant Using the Vascular Network Design

Figure 5:
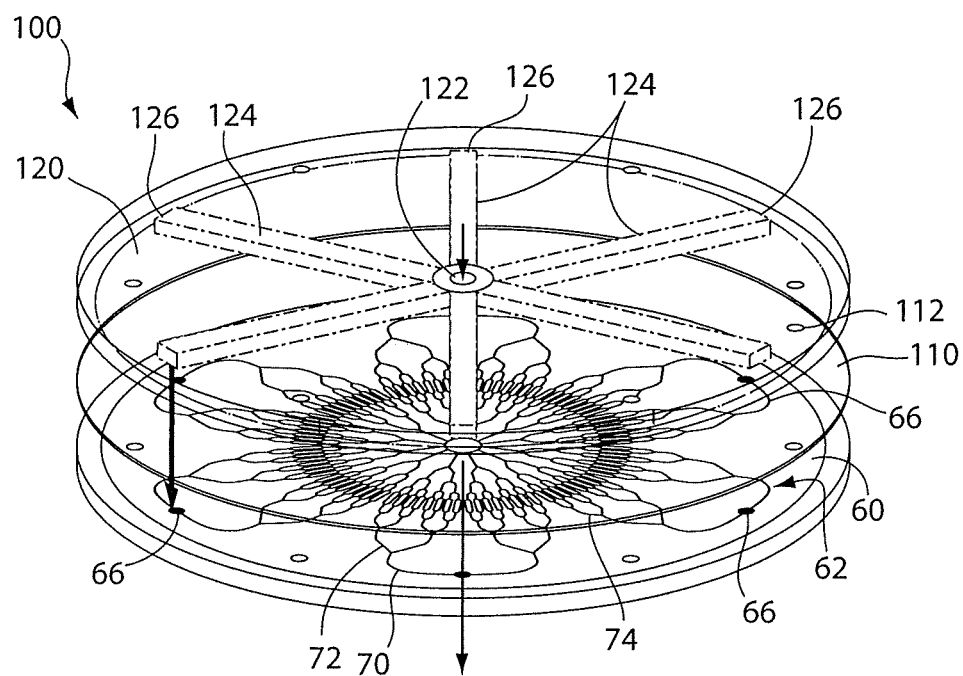
FIG. 5 is an exploded view of implant components using the vascular network design of FIG. 3 in accordance with the subject technology.
Figure 6:
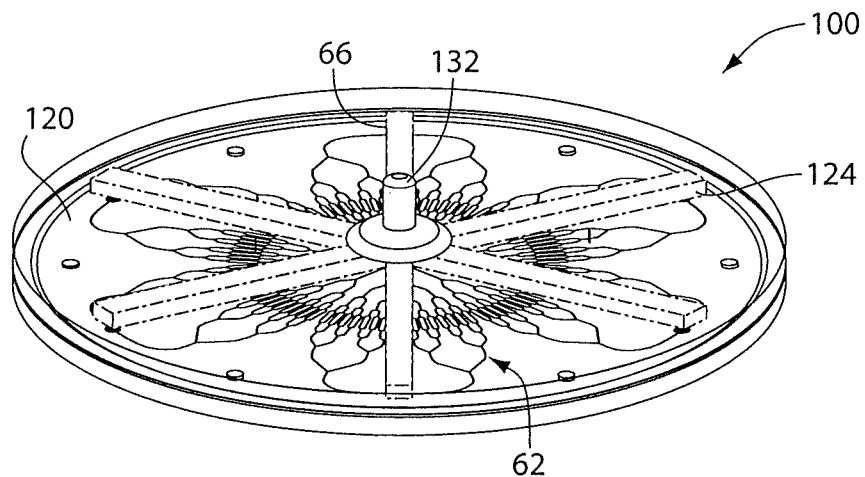
FIG. 6 is an assembled perspective view of the implant of FIG. 5.

Referring now to FIG. 5, an exploded view of an implant 100 using the vascular network design 60 is shown. The implant 100 includes a perforated layer 110 and a header layer 120, which mount on top of the vascular network design 60 to substantially enclose the channels 62 as shown in FIG. 6. The vascular network design 60 has inlets 66 that accept inflow in a direction orthogonal to the branched pattern of channels 62 in the vascular network design 60. In order to direct blood flow from a blood vessel and into the inlets 66 of the vascular network design 60, the header layer 120 distributes blood from a single central inlet 122 via radial channels 124.

On the radially outward end, the radial channels 124 form an opening 126, which aligns with a respective passthrough hole 112 in the perforated layer 110. The passthrough holes 112, in turn, align with the inlets 66 of the vascular network design 60 so that blood flows from the single central inlet 122 to the inlets 66. Blood passes through the header layer central inlet 122, the header layer radial channels 124, the passthrough holes 112 in the perforated layer 110, into the inlets 66 of the vascular network design 60, through the branched pattern of channels 62, and out the central opening 68 of the vascular network design 60.

Figure 7:
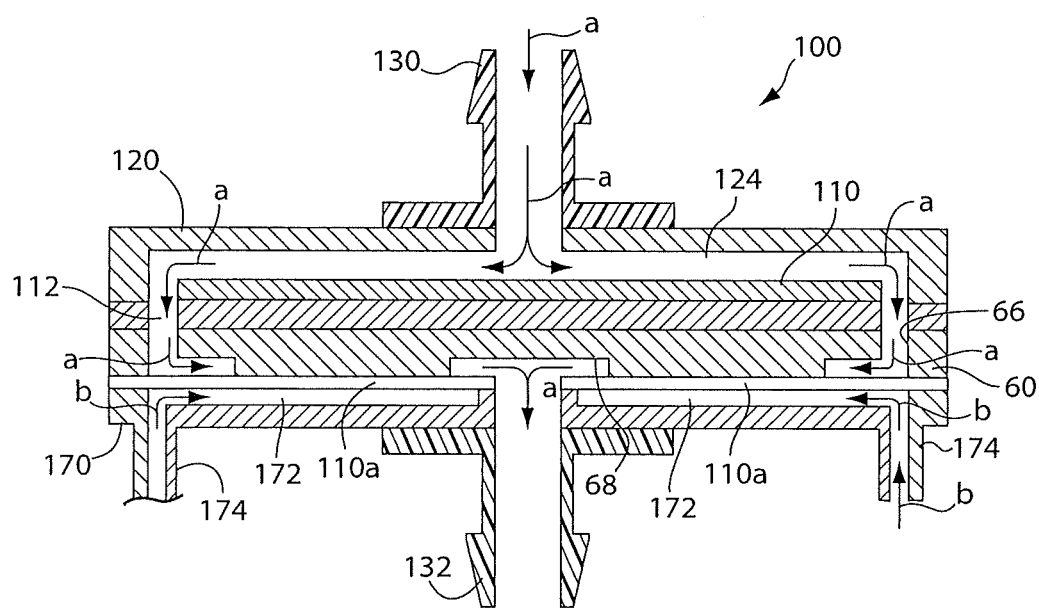
FIG. 7 is an assembled cross-sectional view of an implant using a simple vascular network design in accordance with the subject technology.

Referring to FIG. 7, an assembled cross-sectional view of the implant or scaffold 100 using the simplified vascular network design 60 is shown. The blood enters the scaffold 100 via an inlet nozzle 130. The flow path of the blood is designated by arrows "a". The blood passes through a header layer 120, which separates and directs the blood radially outward through channels 124. The blood then flows through the passthrough hole 112 in the perforated layer 110 and into the inlets 66 of the vascular layer 60. The blood is then directed through the channels 62 of the vascular network design 66, where the blood collects in a central outlet 68. The blood then proceeds through the outlet nozzle 132.

Cells particular to the type of tissue which is being generated (e.g., hepatocytes for liver) are positioned in at least one parenchymal chamber 172 defined by a cellular layer 170. The parenchymal chamber 172 is separated from the vascular network channels 62 by a semi-permeable membrane layer 110a (see FIG. 7). The membrane can be formed from a physiological source (e.g., derived from a living tissue), or from a biologically compatible, nondegradable material such as cellulose, PolyDiMethylSiloxane (PDMS), PolyMethylMethacrylate (PMMA), PolyEtherSulfone (PES), PolySulfone (PS), PolyCarbonate (PC), or from a degradable material such as PLGA, PolyCaproLactone (PCL) or Biorubber, but the invention is not so limited. "Parenchymal cells" include the functional elements of an organ, as distinguished from the framework or stroma. Parenchymal cells can include but are not limited to smooth or skeletal muscle cells, myocytes, fibroblasts, chondrocytes, adipocytes, fibromyoblasts, ectodermal cells, including ductile and skin cells, hepatocytes, kidney cells, liver cells, cardiac cells, pancreatic islet cells, cells present in the intestine, and other parenchymal cells, stem cells including adipose or bone derived mesenchymal stem cells, embryonic stem cells and induced pluripotent stem cells, osteoblasts and other cells forming bone or cartilage, and hematopoietic cells. The cells are not limited to parenchymal cells but can be many other kinds of cells (stem or progenitor cells).

As blood flows though the vascular network layer 60, oxygen and nutrients diffuse across the membrane layer 110a to nourish the cells within the chamber 172. Waste generated by the cells in the chamber 172 can diffuse back across the membrane layer 110a and into the channels 62 of the vascular network layer 60. The chamber 172 may have one or more inlets 174 where the cells can be infused, injected or otherwise inserted into the chamber 172 of the implant 100. The flow path of the cells is designated by arrows "b".

In the embodiment of FIGS. 5-7, there are six radially spaced channels 124 on the header layer 120 that align with six inlets 66 of the vascular network design 66. Single central inlet 122 and outlet 68 align with the nozzles 132, 134 but other configurations may be utilized such as two inlets and two outlets. In another embodiment, there may be four inlets and one outlet. In another embodiment, the number of inlets may be in the range of 1 to 120. In another embodiment, the number of outlets may be in the range of 1 to 120.

The implant 100 has the nozzles 130, 132 for interconnecting with the blood vessels of the body. The inlet nozzle 130 preferably permanently mounts to the central inlet 122 of the header layer 120 and the outlet nozzle 132 permanently mounts to the outlet 68 of the vascular network design 60. The nozzles 130, 132 may utilize a standard artificial vascular graft, such as a PTFE graft. The vascular graft may be secured to the connectors or nozzles 130, 132 by intrinsic compression of the graft around the respective nozzle 130, 132, such as by one or more sutures, clamps, adhesive, locking devices or any combination there of. In another embodiment, a graft may be incorporated directly into the scaffold material without attaching to a nozzle. A graft may be directly secured to a component of the scaffold such as the header layer 120 by one or more sutures, clamps, adhesive, locking devices or any combination there of.

Another Assembled Implant

Figure 8:
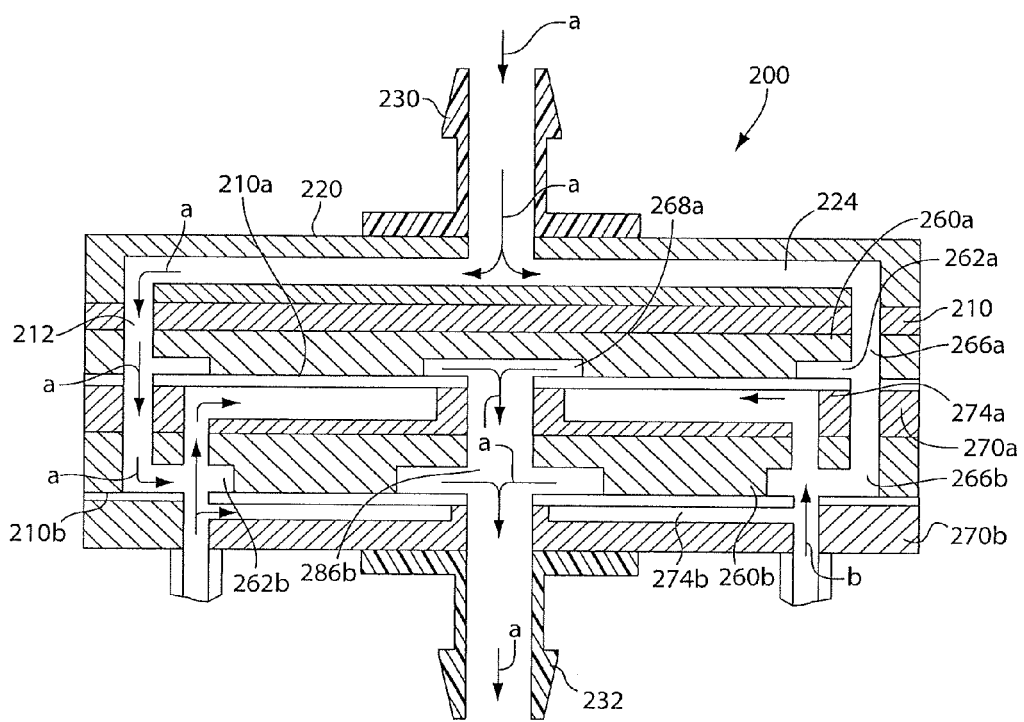
FIG. 8 is cross-sectional view of another implant with multiple vascular layers in accordance with the subject technology.

Referring to FIG. 8, another assembled implant 200 is shown in cross-sectional view. As will be appreciated by those of ordinary skill in the pertinent art, the implant 200 utilizes similar principles to the implant 100 described above. Accordingly, like reference numerals preceded by the numeral "2" instead of the numeral "1" are used to indicate like elements whenever possible. The primary difference of the implant 200 in comparison to the implant 100 is having multiple vascular layers or vascular network designs 260*a*, 260*b* joined to a single header layer 220. Each vascular network design 260*a*, 260*b* couples to respective semi-permeable membrane layers 210*a*, 210*b* and cellular layers 270*a*, 270*b*.

The number of vascular layers may vary such as within the range from 2 to 1000 or more. The number and size of the layers for a particular implant depends on the particular tissue, and the amount of tissue required, and the size of the patient. The number of scaffolds may also be increased to accommodate the needs of the patient.

For multiple vascular layers 260*a*, 260*b*, the inlets 266*a*, 266*b* are redesigned to balance flow between the layers 260*a*, 260*b*. For example, the inlets 266*a*, 266*b* may taper. Alternatively, each vascular layer 260*a*, 260*b* may be fed by only half of the radial channels 224 of the header layer 220. As shown in FIG. 8, the vascular layer 260*a* has inlet holes 266*a* which extend there through in a tapered manner. Thus, blood enters both the channels 262*a*, 262*b* of both vascular layers 260*a*, 260*b* by partially passing through the vascular layer 260*a* into the vascular layer 262*b* below.

In use, blood from the patient enters the implant 200 via the inlet nozzle 230 and proceeds into the header layer 220, where the blood is directed radially via the distribution channels 224. The blood proceeds into through the passthrough holes 212 in the perforated layer 210 and into the inlets 266*a*, 266*b* of the vascular layers 260*a*, 260*b*.

With more than one vascular layer 260*a*, 260*b*, a portion of the blood flow continues vertically downward past the upper vascular layer 260*a*, through respective openings 212*a* in the adjacent semi-permeable membrane layer 210*a* and parenchymal layer 270*a* and into the inlets 266*b* of the lower vascular layer 260*b*. As noted above, to facilitate even distribution of blood between the vascular layers 260*a*, 260*b*, the respective inlets 260*a*, 260*b* and openings 212*a* may taper. Alternatively, select radial channels 224 may feed different vascular layers 260*a*, 260*b*.

Within the vascular layers 260*a*, 260*b*, the blood is directed through the bifurcating channels 262*a*, 262*b* into central collecting outlets 268*a*, 268*b*. The central collecting outlets 268*a*, 268*b* extend through the underlying semi-permeable membrane layers 210*a*, 210*b* and cellular layers 270*a*, 270*b* to discharge the blood through the outlet nozzle 232. The outlet nozzle 232 may direct the blood back into the blood vessel of the patient or to another device for further processing prior to reentry. The semi-permeable membranes 210*a*, 210*b* are adjacent to the vascular network layers 260*a*, 260*b* to separate the vascular network layers 260*a*, 260*b* from the adjacent parenchymal layers 270*a*, 270*b*, but still allow oxygen and nutrients to pass. The parenchymal layers 270*a*, 270*b* form chambers 272*a*, 272*b*, which contain cells corresponding to the tissue which the implant 200 is supplementing or replacing.

In operation, there may be more than one implant or scaffold with a plurality of vascular layer and other layers. The number of implants or scaffolds may be in the range of 1 to 50. In another embodiment the number implants or scaffolds may be in the range of 2 to 8. The implants may have multiple inlets and outlets. For example, a series of inlets may be utilized to supply blood to five vascular layers. The implants may also be connected in a parallel and/or serial configuration between the supply blood vessel and the return blood vessel. Bifurcated vascular grafts may be used as necessary. The number of scaffolds and thus cellular components may be different for each patient and thus a different size or configuration of device may be used for each patient. The chambers 272*a*, 272*b* have two inlets 274*a*, 274*b* where the cells can be infused along the flow path indicated by arrow b, injected or otherwise inserted into the chamber 272*a*, 272*b* of the implant 200.

Implant Performance

Implants 100 according to FIG. 6 have been built and tested. The mold for the vascular layer 60 was built with the EDM process as described previously. The mold for the header layer 120 was built using a traditional milling process. The perforated layer 110 was formed using a standard Petri dish as a mold with a punch process to create the holes 112. The nozzles 132 were created using a traditional machining process. The implant 100 was fabricated from a polydimethylsiloxane (PDMS), a silicone like material, as the material for the header layer 120, the vascular layers 60 and the perforated layer 110. The nozzles 132 may be made with polycarbonate or nylon. For assembly, the header layer 120, the vascular layers 60 and the perforated layer 110 were adhered to one another with oxygen plasma bonding.

Figure 9:
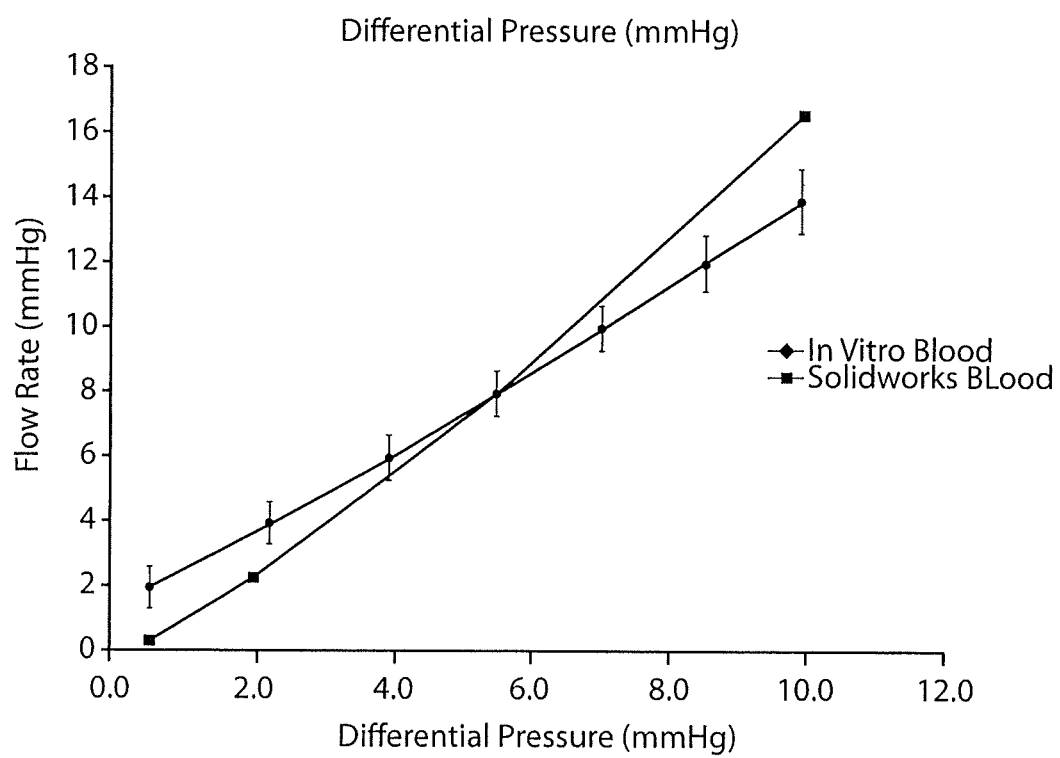
FIG. 9 is a graph of the results of the in vitro blood tests and the analysis of blood flow through the implant of FIG. 6.

The implants 100 were tested with anti-coagulated sheep blood flowing at various flow rates and the inlet pressures of the device were measured. The results were compared to the expected results of the inlet pressure according to CFD analysis. FIG. 9 is a graph of the results of the in vitro blood tests and the analysis of blood flow through the implant 100 using computational fluid dynamics. The in vitro flow results and the CFD results had good correlation, especially at the design point of a 6 mmHg pressure drop across the implant 100. There was a less than 5% variation between the in vitro performance and the expected CFD data.

Another Vascular Layer

Figure 10:
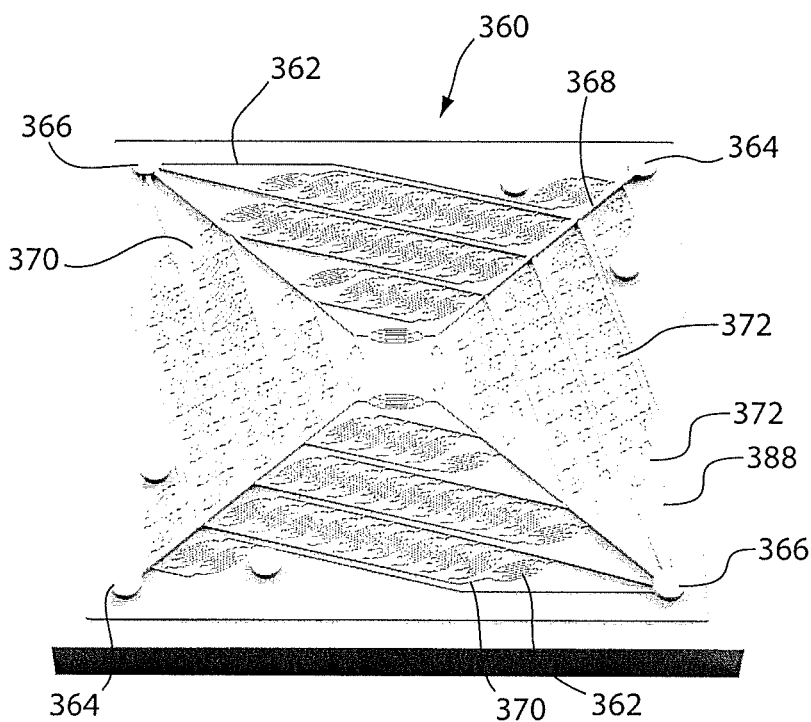
FIG. 10 a perspective view of another vascular network design in accordance with the subject technology.
Figure 11:
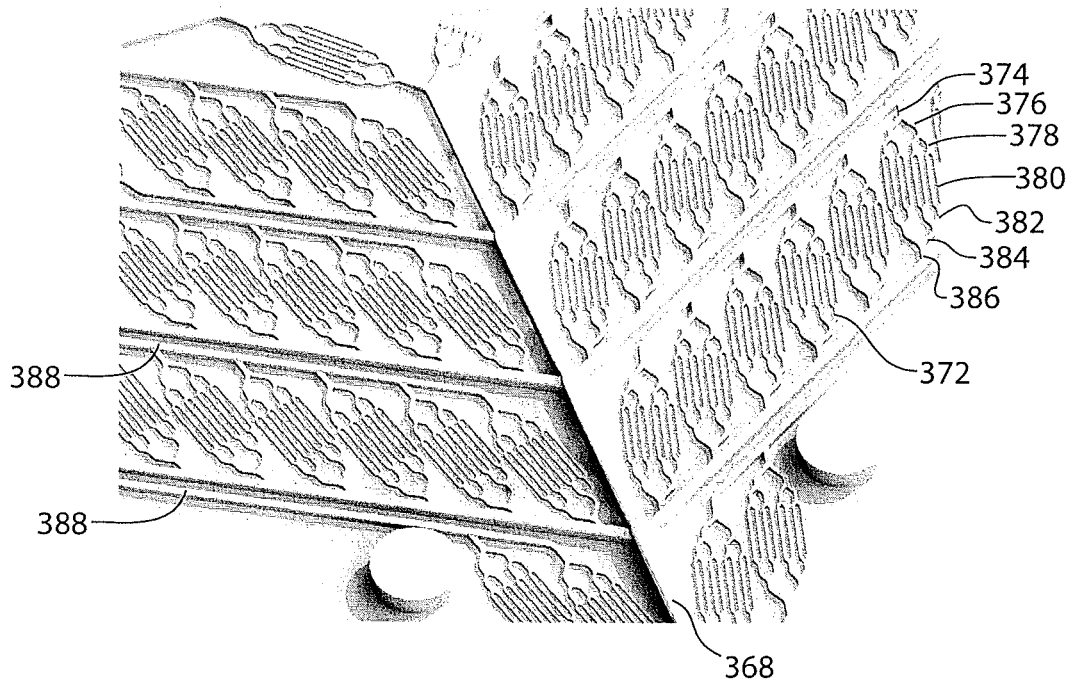
FIG. 11 is a detailed view of the vascular layer of FIG. 10.

Referring to FIGS. 10 and 11, a mold 360 for fabricating another vascular layer is shown in perspective view. The mold 360 consists of raised features where the vascular layer consists of channels. As will be appreciated by those of ordinary skill in the pertinent art, a vascular layer fabricated from mold 360 utilizes similar principles to the vascular layers 60, 160, 260 described above. The primary difference of the vascular layer fabricated from mold 360 in comparison to the vascular layers 60, 160, 260 is an increased density of channels 362.

The branching network of channels 362 in the vascular layer fabricated from mold 360 has two inlets 364 and two outlets 366. A main channel 368 extends from each inlet 364 into daughter channels 370 through a series of trifurcations and ultimately ends in a bifurcation. The daughter channels 370 then branch off into repeating capillary-like subunits 372.

Each subunit 372 is similar although significant variation may be appropriate for certain applications. Each subunit 372 has an initial inlet channel 386 followed by a series of three bifurcations to form a series of successively smaller channels 384, 382, 380 (as best seen in FIG. 11). In one embodiment, the smallest channels 380 are 100 um across and 100 um deep and all of the channels 386, 384, 382, 380 have an aspect ratio of 1:1.

After the smallest channels 380, the subunits 372 coalesce into successively larger channels 378, 376, 374, 388 and the flow collects in two outlets 366. The vascular layer 360 may also have vertically orientated channels at the area of the inlet and outlet so multiple layers can be assembled. It is also envisioned that a resulting implant (not shown) would have a header layer, a perforated layer, nozzles, and/or vascular grafts or tubing leading to vascular grafts and the like. The vascular grafts may further be anastomosed to a blood vessel in the body.

More Implant Performance

The vascular design layer fabricated from mold 360 of FIGS. 10 and 11 was prototyped. The mold 360 created was a positive feature mold. The mold 360 was created in delrin using micromilling technology. Using the mold 360, vascular layers were created using PDMS, which was poured over the mold 360, cured and removed. A second layer (not shown) was bonded to the top of the open vascular network to create a closed vascular network. The two layers were bonded together using oxygen plasma bonding. Silicone tubing was adjoined to the inlets 364 and outlets 366. An external barbed connector and T connector were used to uniformly direct inflow into the two inlet areas and collect outflow from the two outlet areas.

Figure 12:
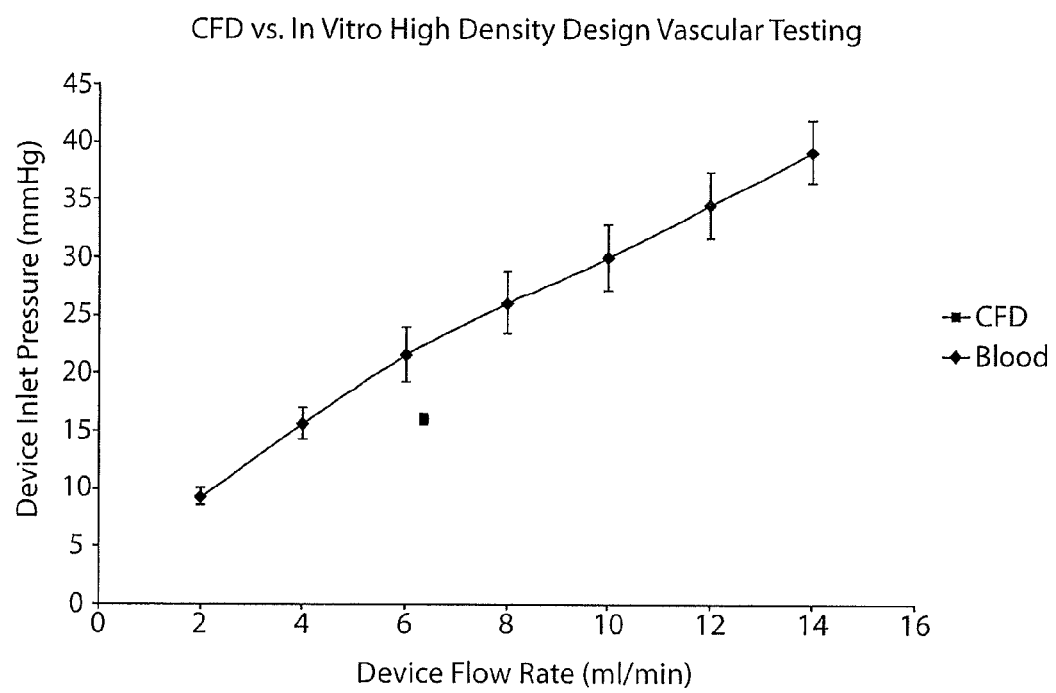
FIG. 12 is a graph of the results of the in vitro blood tests and the analysis of blood flow through an implant using the vascular layer of FIG. 10.

In vitro testing was performed on the vascular network using anticoagulated sheep blood. The blood was pumped through the vascular network using a syringe pump and the inlet pressure to the vascular layer fabricated from mold 360 was recorded over a range of flows. FIG. 12 is a graph of the in vitro testing with blood compared to a data point from CFD analysis. The CFD analysis results for the design point of a differential pressure of 16 mmHG yielded a flow rate of 6.35 mmHg are shown on the graph.

The in-vitro testing required approximately a 20% higher inlet pressure to achieve a similar flow rate. CFD analysis is useful to predict with reasonable accuracy the inlet pressure for a given flow rate through the vascular network fabricated from mold 360. At the flow rate of 6.35 mmHg, the shear stress within the vascular network is controlled within a physiologic range. The flow disturbances are minimized as a result of refining the bifurcation angles and fillets for the design.

The vascular networks disclosed herein demonstrate fundamental design principles which may be useful for generating a wide array of scaffolds for tissue engineering. The designs related to the general design for a liver lobule but could be applied to other organ scaffolds also. The vascular networks may be tailored such that the pressure across the scaffold is matched with the design of the scaffold so there is adequate blood flow in the scaffold to supply oxygen and nutrients to the cells.

A Liver Application

Figure 13:
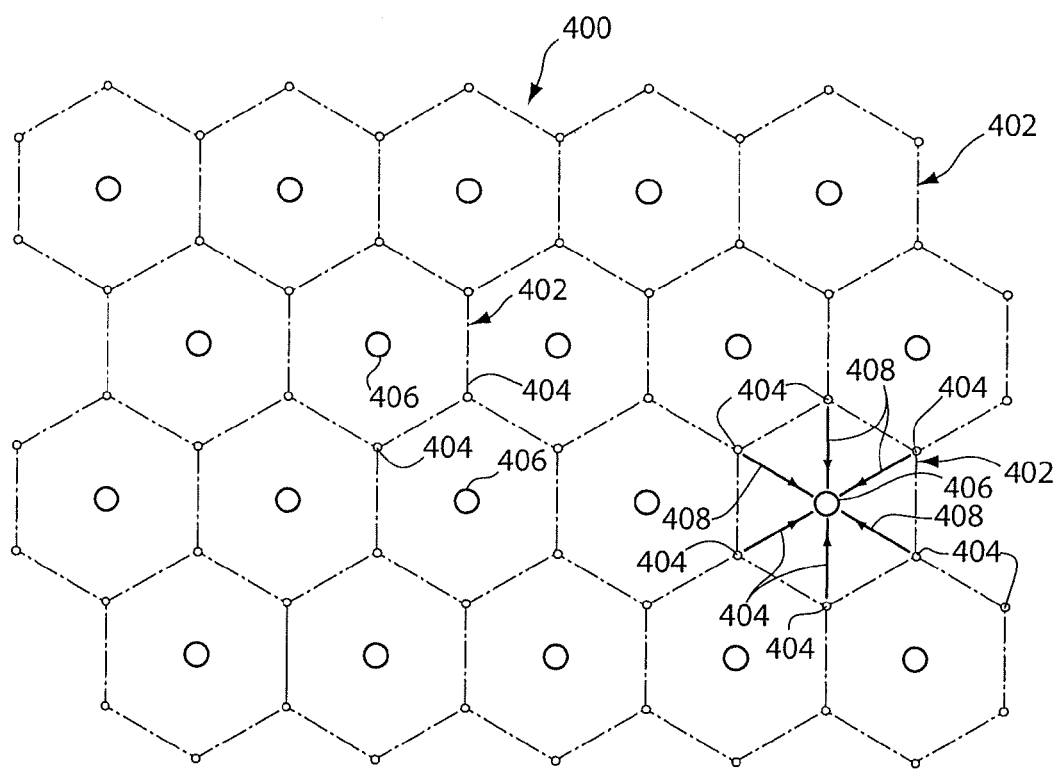
FIG. 13 is a vascular network design which utilizes a repeating polygonal pattern in accordance with the subject technology.

Referring now to FIG. 13, a vascular network design 400 which utilizes a repeating polygonal pattern similar to that of a liver is shown schematically. In another embodiment, the vascular network design may be arranged in a repeating radial pattern similar to that of FIGS. 3-8.

In the liver, polygonal (e.g., hexagonal) liver lobules are arranged in a repeating pattern to achieve a high density configuration. The vascular network design 400 includes multiple polygonal structures 402, each polygonal structure 402 having multiple vascular inputs 404 arranged in a radial pattern around a central vascular output 406. The vascular network design 400 also would include a branching network 408 of channels between the vascular inputs 404 and the central vascular output 406. The branching vascular network design 400 may be similar to the design illustrated in FIGS. 3-8 in other respects.

In another embodiment, the branching vascular network design may follow the design principles as outlined above yet accomplish a high density of vascular channels. For example, the polygonal structures 402 may be positioned adjacent to one another such that the vascular inputs 404 branch into multiple channels which are part of the network of channels for multiple polygonal structures. The diameters of these vascular inputs may be different from vascular inputs positioned at the edge of the design which may only branch into channels which contribute to a single polygonal structure. The polygonal structures may replicate in a way that nine polygonal structures combine to create a single vascular layer. In another embodiment, the number of adjacent polygonal structures which create a vascular layer may be in the range from 1 to 100.

As described above, the flow from the patient may enter the scaffold through a single feature such as an inlet nozzle. The vascular network design 400 may have a header system (not shown), which evenly distributes the inlet flow from a single feature into all of the vascular inputs 404. The header system may incorporate one or more header layers to achieve even flow distribution and incorporate features to minimize thrombus formation. In a similar fashion, there may be a header system which collects the flow from the vascular outputs 406 and diverts it into a single outlet feature such as a nozzle.

Figure 15:
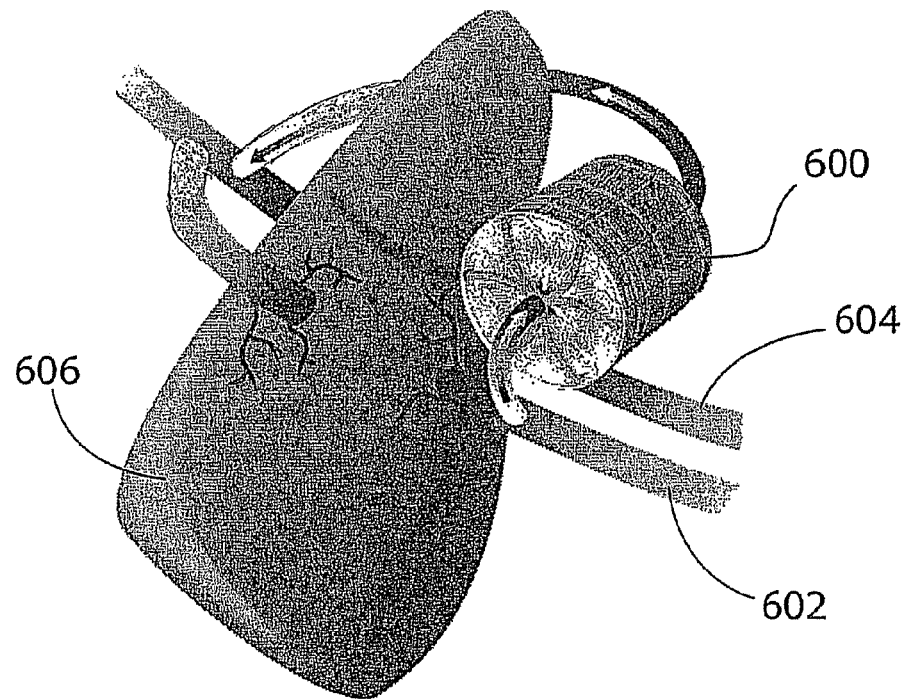
FIG. 15 is an implant in accordance with the subject technology in place as a liver assist device.

Referring to FIG. 15, an implant 600 in accordance with the subject technology is shown in place as a liver assist device. The tissue engineered implant 600 is connected between the portal vein 602 and the inferior vena cava 604 of the liver 606. In a patient with liver failure, their portal pressure is usually 10 mmHg or higher and the inferior vena cava pressure is often 0-2 mmHg. Thus, the differential pressure (e.g., the difference of the inlet and outlet pressures) may be 8 mmHg. Thus the flow through the scaffold for a tissue engineered liver must be adequate with approximately low pressures.

In another embodiment, a vascularized scaffold for a tissue engineered liver may incorporate portal venous blood inflow and arterial blood inflow into the scaffold and may have a common venous outflow. The scaffold may be analogous to the human liver which has both portal venous and hepatic artery inputs. The hepatic artery primarily supports the biliary cells within the liver and hepatocytes in the outer portion of the hepatic lobule. There may be arterial inputs within a vascular layer in the same region as the portal venous inputs. The resulting branching network from the arterial inputs may not extend to and connect directly with a central output. The arterial network may connect directly with the branching network from the portal vein.

In still another embodiment, the arterial vascular network would go through sufficient branching and have sufficient pressure drop as to not significantly change the pressure within the portal venous channels when connected thereto. The branching arterial network may be a different layer, or a different plane or otherwise remote from the branching portal vein network. The branching arterial network may also connect directly with a central draining output which may also include output from the portal venous network.

In another embodiment, if a vascularized scaffold is created for a tissue engineered lung, the vascularized scaffold may be positioned between the pulmonary artery and the left atrium. Depending on the degree of pulmonary hypertension of a patient with end stage lung disease, the mean differential pressure between the pulmonary artery and left atrium may be 12 to greater than 20 mmHg. A vascularized lung scaffold may need to have sufficient flow for a differential pressure in this range. In another embodiment, the vascularized scaffold may be tailored to create at least a portion of a tissue engineered kidney, pancreas, skeletal muscle, heart, intestine, bladder, tongue or soft tissue.

A Lung Application

Figure 16:
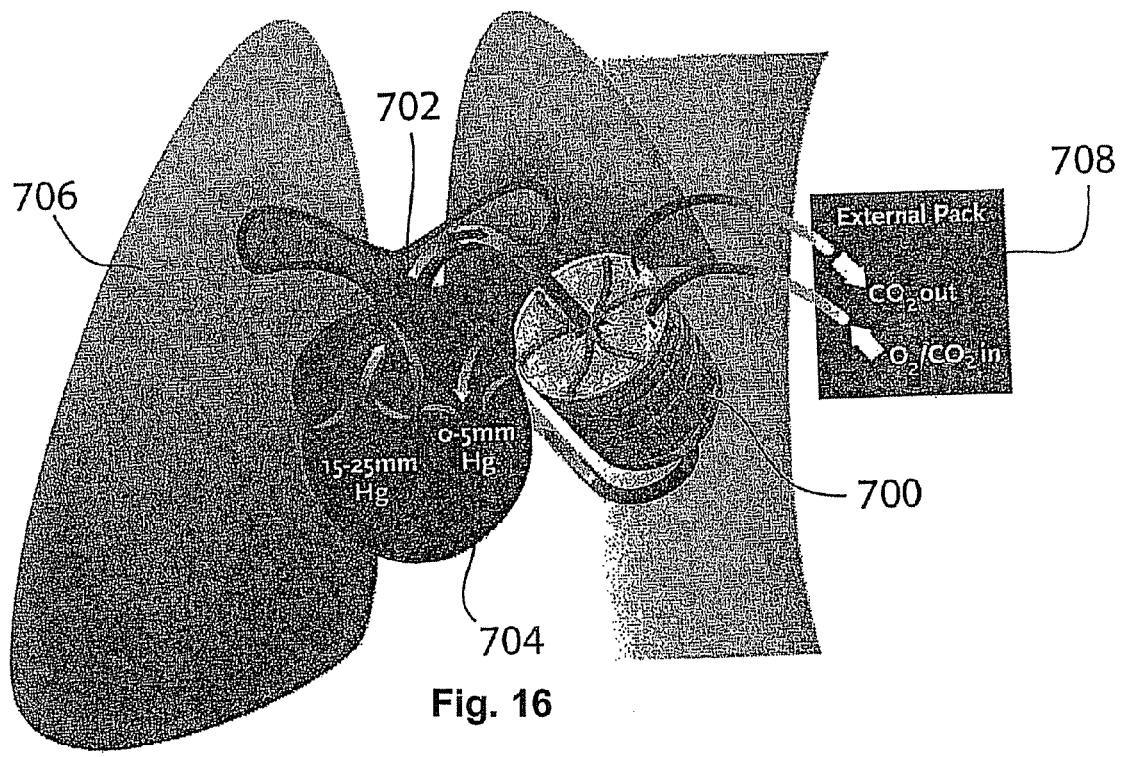
FIG. 16 is an implant in accordance with the subject technology in place as a lung assist device.

Referring to FIG. 16, an implant 700 in accordance with the subject technology is shown in place as a lung assist device. The tissue engineered implant 700 is connected between the pulmonary artery 702 and the left atrium of the heart 704. In this position, the tissue engineered lung implant 700 augments the function of the lung 706. An external pack 708 provides oxygen, air or another gas or gas mixture to the implant 700. In use, blood flows through the implant 700 including the vascular layer(s) as described in FIG. 6. The oxygen or other gas flows through the parenchymal layer, separated from the vascular layer by a gas permeable membrane. Oxygen diffuses from the parenchymal layer across the membrane and into the blood. Likewise carbon dioxide diffuses from the blood across the membrane and into the parenchymal layer. The flow of gas through the parenchymal layer washes the carbon dioxide out of the parenchymal layer. This exchange of oxygen and carbon dioxide between the blood and parenchymal layer performs the fundamental functions of a lung, which is the oxygenation of blood and removal of carbon dioxide from the blood. For the tissue engineered lung application, the semi-permeable membrane 110a of FIG. 7 is permeable to oxygen and carbon dioxide. The membrane can be porous, non-porous or a combination of porous and non-porous portions. For example, the membrane may be a porous material such as polycarbonate covered with a very thin non-porous but gas permeable material such as silicone. In another embodiment, the membrane may be a resorbable material such as collagen.

Furthermore, the membrane may be covered with cells. In one embodiment the portion of the membrane adjacent to the vascular layer may be covered with endothelial cells. In another embodiment, these endothelial cells may be lung endothelial cells or non-lung endothelial cells which express carbonic anhydrase on their membranes. Carbonic anhydrase is an enzyme which converts bicarbonate into carbon dioxide. In the blood most of the carbon dioxide occurs in the form of bicarbonate. In the lung, the bicarbonate is quickly converted to carbon dioxide by carbonic anhydrase and then can diffuse into the air spaces of the lung, the alveoli. In another embodiment, the membrane can be covered with endothelial cells as described above on the side adjacent the vascular layer and covered with lung epithelial cells (Type I, Type II or both) on the parenchymal side of the membrane. For the tissue engineered lung application, the total surface area of the vascular layer and parenchymal layer interface is sufficient to have exchange of oxygen, carbon dioxide or both to augment the lung function of a patient.

In one embodiment, the scaffold may be placed within the body as previously described. In another embodiment, the scaffold may be placed outside the body with vascular or other connections (e.g., biliary, respiratory and the like) interfacing with the scaffold by protruding through the skin or another opening in the body. An externally placed scaffold may be useful for temporary support of an organ such as the liver or lung. In another embodiment, a pump may be may be positioned in the circuit between the patient and an external scaffold to augment the flow of blood through the scaffold. Types of pumps might include a roller pump, centrifugal pump or piston pump. For example, a temporary lung assist device may interface with a patient in a such a way that two separate venous catheters supply the blood to the scaffold and return blood from the scaffold. Due to inadequate pressure drop between two veins, an external pump may be added to effect blood flow through the scaffold.

The material for the vascular network may be composed of a material which allows the attachment of cells. In another embodiment, the material may allow the attachment of vascular cells such as endothelial cells, smooth muscle cells, and fibroblasts. In another embodiment, the material may be a non-resorbable material, a resorbable material or a combination of non-resorbable and resorbable materials. In another embodiment the material may be a combination of resorbable materials or a combination of non-resorbable materials. A representative, but not exhaustive, list of resorbable materials or biodegradable polymers for construction of vascular scaffolds is shown in Table 1.

TABLE 1

Aliphatic polyesters
Bioglass
Carboxymethylcellulose
Cellulose
Chitin
Citrate
Collagen
Copolymers of glycolide
Copolymers of lactide
Elastin
Fibrin
Hydrogel
Modified proteins
Nylon-2
PLA/polyethylene oxide copolymers
PLA-polyethylene oxide (PELA)
Poly (amino acids)
Poly (trimethylene carbonates)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)

TABLE 1-continued

Polyesteramides
Polyesters of oxalic acid
Polyethylene Glycol
Polyethylene Oxide
Polyglycan Esters
Poly(Glycerol Sebacate)
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers
Glycolide/l-lactide copolymers (PGA/PLLA)
Glycolide/trimethylene carbonate copolymers (PGA/TMC)
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
PHBA/γ-hydroxyvalerate copolymers (PHBA/HVA)
Poly hydroxyalkanoate polymers (PHA)
Poly-β-hydroxypropionate (PHPA)
Poly-β-hydroxybutyrate (PBA)
Poly-σ-valerolactone In another embodiment, the thickness of the material of the scaffold may be very thin. The thickness of the scaffold material used to create a patterned vascular layer may be in the range of 0.1 um to 1000 um thick. In another embodiment, the thickness of the scaffold material may be in the range of 1 um to 10 um thick. The scaffold or supporting tissue of organs often comprises collagen as an abundant component.

Collagen Layers

An embodiment of this construct may include collagen films as the primary scaffold material. Collagen is the primary component of the extracellular matrix in solid organs and other tissues including blood vessels. The strength of collagen is highlighted by the durability of human tissues. For example, human veins typically have a burst pressure of several thousand mmHg yet are so thin they are partially transparent. The strength of thin collagen films may allow the creation of a vascularized scaffold with minimal scaffold component mass to maximize the amount of functional tissue present in a particular volume of the scaffold. Cells readily adhere to collagen and may adsorb and remodel the collagen to optimize the scaffold prior to or following implantation.

Collagen may also be constructed in a thin film, sheet, or other porous or non-porous construct. In a embodiment, a collagen thin film, sheet or other construct will have a degree of porosity. This porosity may be uniform in size or spacing. The pores sizes may only allow small molecule in the range 1 to 500 kilodaltons. In another embodiment, the pores may be in the range of 1 micron to 100 microns. The porosity of the collagen network may be sufficient to allow the diffusion of oxygen, carbon dioxide, proteins, carbohydrates, fats, drugs, or any other biologically active across the collagen network. The porosity of the collagen may be adjusted to meet the required diffusion for a particular target tissue such as the heart, liver or lung.

Given the porosity of the collagen, an additional membrane between the vascular channel and the cells of the tissue or organ may not be required. The cells of the target tissue, for example, myocardial cells, could be placed directly on the vascular network. A second layer of vascular network could be added on top of the cells so each area with cells of the target tissue may be in contact with more than one vascular network layer. Successive vascular networks could be staggered in such a way that the vascular network patterns are not precisely overlying one another. The out of alignment arrangement may allow the cells of the tissue between the vascular network layers to be closer to a respective channel than if the layers were precisely aligned. The collagen films may be very thin and may be patterned to form the desired branching patterns and chambers.

Manufacturing a vascular network pattern out of collagen may be achieved in a number of methods. A collagen film, sheet or other thin structure may be formed into a pattern consistent with a vascular network pattern, such as the networks shown above. Once a patterned network is created in collagen, a second collagen film, sheet or other thin structure which is not patterned may be bonded to the patterned collagen network, thus creating a sealed or closed collagen vascular network which has a network of channels consistent with a desired network design. The patterned network created in collagen may have channels, which are the desired depth of the final channel.

In another embodiment, the patterned network created in collagen may have half of the desired depth of the final channel. The patterned network may be bonded to a similarly patterned network, where the result is a closed collagen vascular network with the desired depth of the final channel. Although the closed collagen vascular network may be created in a such a manner that the cross section of the channel is rectangular at one point in the fabrication, upon filling the vascular network with a fluid, the resulting cross section of the channel may be circular, oval, elliptical or may retain a rectangular shape.

Figure 14:
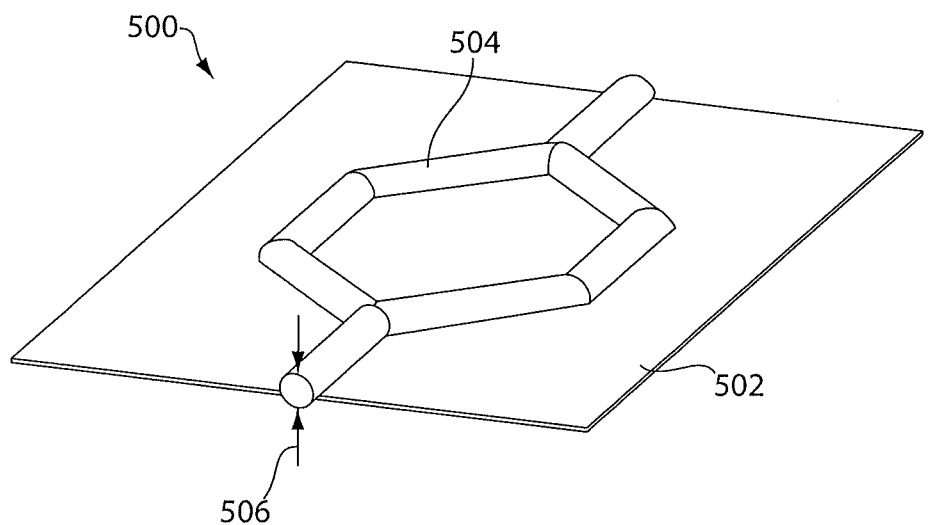
FIG. 14 is a portion of a vascular network created with a collagen film in accordance with the subject technology.

Referring to FIG. 14, a portion 502 of a vascular network 500 created with a collagen film, sheet or other thin structure is shown. The portion 502 shows a vascular channel 504 with a single bifurcation design. The collagen material 502 has a total thickness, which may be less than the inner diameter 506 of the channel 504. For example, the thickness of the collagen material or portion 502 may be 10 um and the inner diameter 506 of the vascular channel 504 may be 100 um. The vascular network 500 could be manufactured by creating a patterned collagen film or sheet and bonding an unpatterned collagen film or sheet thereto. The vascular network 500 could also be manufactured by bonding two patterned collagen films together as described above.

The manufacturing of a patterned collagen film may accomplished by starting with a positive mold of the desired vascular network. Such a mold has ridges corresponding to the desired channels of the network. It is a negative of the desired structure. A solution, suspension, colloid or other mixture containing collagen may be poured or otherwise placed over the mold. The collagen mixture may then be air dried or vacuum dried. The drying may occur at or above ambient temperature.

After drying, the collagen film then may be separated from the mold resulting in a patterned collagen film. In another embodiment, the collagen mixture may then be gelled by incubation. The resulting gel may be air dried or vacuum dried. The resulting collagen film may be removed from the mold and retain the pattern and features of the mold. A patterned collagen film may be bonded to a flat or other patterned collagen film using adhesive, dehydrothermal cross-linking adjacent collagen sheets, chemically cross-linking adjacent collagen sheets or photochemically cross-linking collagen with a photosensitizing dye. In the embodiment where a patterned film is placed adjacent to an unpatterned or flat collagen film, the patterned film or the unpatterned may be dry, partially dry or hydrated. A degree of hydration of one or more of the films may result in a desirable degree of coaptation of the non-channeled portion of the patterned film to the corresponding flat film.

Thin films (e.g., having thicknesses of less than 10 um) that are patterned or unpatterned may have peripheral support elements to aid in handling. These elements may assist in the handling of thin films during patterning, coaptation, bonding, stacking and attachment of other components in the manufacturing process. The peripheral support elements may include a mesh material, a filament, a plurality of filaments, a substantially solid material or a solid material. The support elements may be temporary and removed prior to implantation of the scaffold within the body of a living being. The support elements may be resorbable or non-resorbable and may be implanted into the body of a living being within the scaffold. The inlet tubes and header components may also be composed of collagen materials including collagen tubes.

The collagen components may be formed of collagen from bovine, porcine, equine, ovine, human or other mammalian sources. Any collagen type or any combinations of collagen types may be used. In another embodiment, the patterned or unpatterned films may be composed of a mixture of collagen and non-collagen components. In another embodiment, the films may be a mixture of collagen types (e.g., types I, III, IV and VII). In another embodiment, the non-collagen components may be materials derived from natural membranes or one or more extracellular matrix proteins or any other naturally occurring portions or components of the extracellular tissues in a living being. These extracellular matrix proteins or components may be one or more of the following; fibrin, elastin, fibronectin, laminin, hyaluronic acid, heparin sulfate or chondrotian sulfate. In one embodiment, a patterned sheet which is bonded to an unpatterned sheet may be of different material composition than the unpatterned sheet. In another embodiment, the material for the patterned and flat films is a combination of collagen type I, collagen type IV, fibrin and fibronectin.

In another embodiment, scaffold in accordance with the descriptions above may be used to ascertain the efficacy of drugs on human cells. For example, a scaffold may be fabricated to determine metabolism of a test agent in a certain kind of tissue. The scaffold could incubate the test agent and an enzyme, and form an enzyme-substrate complex between the enzyme and the test agent. As a result, one could detect one or more metabolites of the test agent. For additional example, see U.S. patent application Ser. No. 10/215,600 filed on Aug. 9, 2002 and Ser. No. 11/183,115 filed on Jul. 15, 2005.

INCORPORATION BY REFERENCE

All patents, published patent applications and other references disclosed herein are hereby expressly incorporated in their entireties by reference. It should be understood that the foregoing disclosure and description of the present invention are illustrative and explanatory thereof and various changes in the size, shape, and material composition, as well as in the description of the embodiments, may be made without departing from the spirit of the invention as defined by the appended claims.

What is claimed is:

1. An artificial vascular layer comprising:
a substrate defining a network of channels having at least one input channel and at least one output channel and a plurality of branching intermediate channels at least partially connecting the at least one input channel and the at least one output channel, each channel having a height, a length, and a width, and a diameter, wherein
the intermediate channels are formed in accordance with Murray's law by varying said height and width of the intermediate channels with respect to adjacent channels, and the length of the intermediate channels with a smallest diameter have a biomimetic length.

2. The artificial vasculature layer of claim 1, wherein the lengths of the intermediate channels with the smallest diameter conform to a polynomial equation relating mammalian vessel length to vessel diameter.

3. The artificial vasculature layer of claim 1, wherein at least one input channel trifurcates at least once.

4. The artificial vasculature layer of claim 1, wherein at least one of the intermediate channels has a bottom extending between opposing side walls to form bottom corners and further comprising fillets in the bottom corners.

5. The artificial vasculature layer of claim 1, further comprising a transition area at about an intersection between at least two of the channels having different dimensions, wherein the transition area is configured to reduce shear stress at the intersection.

6. The artificial vasculature layer of claim 5, wherein the transition area comprises a ramp providing a transition from a bottom of a first of the at least two channels to a bottom of a second of the at least two channels, wherein the first of the at least two channels has a first height, and the second of the at least two channels has a second height, different from the first height.

7. The artificial vasculature layer of claim 5, wherein the transition area comprises a fillet providing a transition from a bottom of a first of the at least two channels to a bottom of a second of the at least two channels, wherein the first of the at least two channels has a first height, and the second of the at least two channels has a second height, different from the first height.

8. The artificial vasculature layer of claim 1, wherein the substrate comprises a collagen substrate.

9. The artificial vasculature layer of claim 8, wherein the collagen substrate comprises elastin.

10. The artificial vasculature layer of claim 8, wherein the collagen substrate comprises fibronectin.

11. The artificial vasculature layer of claim 1, comprising a collagen film deposited on the substrate.

12. The artificial vasculature layer of claim 1, wherein the substrate comprises silicone.

13. The artificial vasculature layer of claim 1, wherein an aspect ratio of the
intermediate channels is 1:1.

14. A device comprising:
a first substrate defining a vasculature layer having at least one input channel, at least one output channel, and at least two intermediate channels at least partially connecting the at least one input channel and the at least one output channel, each channel having a height, a length, and a width, and a diameter;
a second substrate defining a cellular layer coupled to first substrate, the cellular layer defining a chamber for holding parenchymal cells and configured to receive oxygen and nutrients from a fluid in the vascular layer; and a semi-permeable membrane separating the vasculature layer and the cellular layer;

wherein:

the intermediate channels are formed in accordance with Murray's law by varying said height and width of the intermediate channels with respect to adjacent channels, and the length of the intermediate channels with a smallest diameter have a biomimetic length.

15. The device of claim 14, wherein the semi-permeable membrane is configured to allow exchange of at least one small compound between a fluid or gas in the vascular layer and parenchymal cells in the chamber.

16. The device of claim 15, wherein the fluid is one of blood, plasma, and media.

17. The device of claim 15, wherein the at least one small compound is selected from the group consisting of oxygen, nutrients, carbon dioxide and waste.

18. The device of claim 14, wherein the vasculature layer and cellular layer comprise a portion of a medical device for assisting or replacing an organ.

19. The device of claim 14, comprising a distribution network coupled to a nozzle for accepting an input fluid, the distribution network including a plurality of distribution channels for distributing the accepted fluid among the at least one input channel.

20. The device of claim 14, wherein the parenchymal cells are derived from stem cells or from an organ selected from the group consisting of heart, liver, pancreas, intestine, brain, kidney, reproductive tissue, lung, muscle and bone marrow.

21. A method of manufacturing artificial vasculature, comprising:

providing a substrate;

forming, in the substrate, a network of channels, including at least one input channel, at least one output channel, and at least two intermediate channels at least partially connecting the at least one input channel and the at least one output channel, each channel having a height, a length, and a width, and a diameter, wherein the intermediate channels are formed in accordance with Murray's law by varying said height and width of the intermediate channels with respect to adjacent channels, and the length of the intermediate channels with a smallest diameter have a biomimetic length.

22. The method of claim 21, comprising forming the at least one input channel, the at least one output channel, and the intermediate channels at least in part through a machining process.

23. The method of claim 21, comprising:

calculating a bifurcation angle for use in bifurcating an input channel into intermediate channels based on the diameter of the respective intermediate channels; and forming said channels using the calculated bifurcation angle.

24. The method of claim 23, wherein forming said channels using a machining process comprises machining a mold defining the inverse of the channels.

25. The method of claim 23, wherein forming said channels using a machining process comprises electrical discharge machining the substrate.

26. The method of claim 21, wherein forming the network of channels comprises generating an initial vasculature layer;

analyzing the initial vasculature based on desired parameters selected from the group consisting of a characteristic of a specific fluid, an input pressure, an output pressure, an overall flow rate, and combinations thereof to determine shear stress and velocity within the network of channels;

measuring the shear stress and the velocity and comparing the obtained values to predetermined values; and determining if either of the shear stress or the velocity are greater than or less than the predetermined values.

27. The method of claim 26, comprising modifying the channels by adjusting an associated shear stress and velocity to reduce thrombus formation within the channels based on the comparison to the predetermined parameters.

28. The method of claim 21, comprising:

forming a cell layer defining a chamber for holding parenchymal cells;

coupling the cell layer and the substrate;

seeding cells into the chamber; and nourishing the cells seeded into the chamber by passing blood through the network of channels in the substrate.

29. The method of claim 28, comprising providing a semi-permeable layer between the network of channels and the cell layer.

30. The method of claim 29, wherein the semi-permeable layer has pores of between about 0.01 μm to about 20 μm.

31. A method of at least partially replacing the function of an organ in a patient, comprising:

providing an artificial organ device comprising a first substrate coupled to a second substrate and separated by a semi-permeable membrane; wherein the first substrate defines a vasculature layer having at least one input channel, at least one output channel, and at least two intermediate channels at least partially connecting the at least one input channel and the at least one output channel, each channel having a height, a length, and a width, and a diameter, the intermediate channels are formed in accordance with Murray's law by varying said height and width of the and the length of the intermediate channels with a smallest diameter have a biomimetic length, and the a second substrate defines a cellular layer coupled to the first substrate, the cellular layer defining a chamber for holding parenchymal cells and configured to receive oxygen and nutrients from a fluid in the vascular layer; and coupling the artificial organ device to at least one arterial vessel and one venous vessel of the patient.

32. The method of claim 31, comprising coupling the device to the blood supply of the patient.

33. The method of claim 32, wherein coupling the device to the blood supply comprises coupling the blood supply of the patient to a distribution network for distributing blood from the patient to a plurality of inlet channels.

34. The method of claim 33, wherein the artificial organ comprises a plurality of vasculature layers, and the distribution network couples the blood supply of the patient to at least one inlet of each of the vasculature layers.

* * * * *